(12) United States Patent
Katz

(10) Patent No.: US 6,543,454 B1
(45) Date of Patent: Apr. 8, 2003

(54) METHOD FOR ASSESSING THE SEVERITY OF NON-ADDICTIVE AND ADDICTIVE PSYCHOACTIVE CHEMICAL RELATIONSHIPS

(76) Inventor: Pete S. Katz, 22128 Briarcliff Dr., Spicewood, TX (US) 78669

( * ) Notice: Subject to any disclaimer, the term of this patent is extended or adjusted under 35 U.S.C. 154(b) by 0 days.

(21) Appl. No.: 09/414,779

(22) Filed: Oct. 8, 1999

Related U.S. Application Data

(60) Provisional application No. 60/103,596, filed on Oct. 9, 1998.

(51) Int. Cl.$^7$ ................................................ A61B 19/00
(52) U.S. Cl. ...................................................... 128/898
(58) Field of Search .......................... 600/300; 128/898, 128/899; 434/236

(56) References Cited

U.S. PATENT DOCUMENTS 5,692,501 A  * 12/1997  Minturn ...................... 600/300

OTHER PUBLICATIONS

"Appendix 6: Drug Abuse Screening Test".
Drug Abuse Screening Test Questions.
Gavin, Douglas R., et al., "Diagnostic Validity of the Drug Abuse Screening Test in the Assessment of DSM–III Drug Disorders", British Journal of Addiction, 1989, vol. 84, pp. 301–307.
"Michigan Alcoholism Screening Test" [Descriptive Summary].
"Mortimer–Filkins Evaluator's Training Manual".
"Mortimer–Filkins Questionnaire" [Instructions Sheet and Questions].
"Mortimer–Filkins Test for Identifying Problem–Drinking Drivers" [Description].
Selzer, Melvin L., "The Michigan Alcoholism Screening Test: The Quest for a New Diagnostic Instrument", Amer. J. Psychiat., Jun., 1971, vol. 127, pp. 1653–1658.
Skinner, Harvey A., "The Drug Abuse Screening Test", Addictive Behaviors, 1982, vol. 7, pp. 363–371.
"Summary", Drug Abuse Screening Test (DAST 20) [Brief Summary].
"User's Guide: A Quick Reference for Administration and Scoring", Substance Abuse Subtle Screening Inventory (SASSI–3).
Webb, Gloria R., et al., "The Reliability and Stability of the Mortimer–Filkins Test", J. Stud. Alcohol, 1992, vol. 53, pp. 561–567.
American Psychiatric Association, Washington, D.C., Diagnostic and Statistical Manual of Mental Disorders, Fourth Edition, DSM–IV, "Substance–Related Disorders", pps. 175–183 (1994).
Fureman, Barbara, et al., "A Guide to Training and Supervising ASI Interviews Based on the Past Ten Years," Addiction Severity Index, Fifth Edition with Preface, Apr. 1990, pp. 1–42 (including assessment guidelines).

* cited by examiner

*Primary Examiner*—Max F. Hindenburg
*Assistant Examiner*—Brian Szmal
(74) *Attorney, Agent, or Firm*—Morgan, Lewis & Bockius LLP

(57) ABSTRACT

A system for assessing the severity of non-addictive and addictive psychoactive chemical use disorders is disclosed.

11 Claims, No Drawings

METHOD FOR ASSESSING THE SEVERITY OF NON-ADDICTIVE AND ADDICTIVE PSYCHOACTIVE CHEMICAL RELATIONSHIPS

PRIOR INVENTION

This specification is based on prior U.S. Provisional Patent Application Serial No. 60/103,596 filed Oct. 9, 1998, which is incorporated by reference in its entirety.

FIELD OF THE INVENTION

The present invention relates generally to systems and methods for analyzing and assessing a subject's relationships with mood altering chemicals. This method is described as The Chemical Use/Misuse Continuum (CUMC) Diagnostic System.

NOTE: A portion of the disclosure of this patent document contains material that is subject to copyright protection. The copyright owner has no objection to the facsimile reproduction by anyone of the patent disclosure, as it appears in the Patent and Trademark Office patent and Trademark Office patent files or records, but otherwise reserves all copyright rights whatsoever.

BACKGROUND OF THE INVENTION

There has long been an interest in how to deal with people that have alcohol and/or other drug (AOD) use problems. Enmeshed in this dilemma has been the ongoing debate and theoretical evolution in the counseling and medical fields towards developing a working definition that captures the complex nature of substance abuse disorders. Controversy remains regarding chemical dependency's disease status, its etiology and the nature of its development. It is clear that those who are afflicted with the disorder suffer varying degrees of misery, the effects of which are also shared by society. However, objective, consistent and quantifiable methods for properly approximating the severity of such substance misuse have not yet been developed and widely accepted.

In the early 1950s, the American Medical Association (AMA) recognized alcoholism as a disease. However, the medical establishment's frustration with treating and even diagnosing the disorder has marked its historically troubled involvement in dealing with this universally acknowledged health problem. The human and financial costs to our society are overwhelming. There is also an alarming discrepancy between the size of the problem, i.e., the number of patients hospitalized for alcohol/other drug mediated physical complications, and the proportion of curriculum time allocated to addiction by the medical schools in the training of the average medical student.

The first Diagnostic and Statistical Manual (DSM-I) published in 1952, by the American Psychiatric Association (APA) defined alcoholism as an "addiction" to alcohol. The DSM-II, DSM-III, DSM-III-R, and the DSM-IV followed the DSM-I in 1968, 1980, 1987, and 1994, respectively. Each new version provided a more updated interpretation of the disorder by the medical establishment. Despite this evolution, the DSM-IV diagnostic criteria still reflects an unreasonable level of subjectivity, with numerous incidences of non-specific terminology.

The DSM manuals are often considered to be difficult to apply as a diagnostic model, with a high level of scientific confidence, other than to making the most general of ill defined separations between three categories of "non-problem", "problem" (i.e., substance abuse disorder), and "addictive" (substance dependence disorder) user categories.

A variety of screening instruments have been developed to facilitate making the diagnoses of substance use disorders in AOD using subjects and patients. However, each by their inherent nature reflect certain biases. It has been postulated that utilizing multiple screening instruments can mitigate these biases to some degree. Therefore, this invention includes, but is not limited to, the results from a battery of the following screening instruments:

1. Michigan Alcohol Screening Test (MAST)
   Melvin L. Selzer, M.D.
   University of California, San Diego
   6967 Paseo Laredo
   La Joya, Calif. 92037
   This MAST is a 24-item questionnaire designed to differentiate alcoholics from non-alcoholics.
2. Numerical Drinking Profile (NDP)
   This instrument is a six-question addendum to the MAST. The final determination of the NDP score is affected by the MAST score result. Therefore, the MAST must be scored before the NDP score can be determined.
3. The Drug Abuse Screening Test (DAST)
   Dr. David Timken
   Alcohol and Drug Abuse Division
   Colorado Department of Health
   4210 E. 11$^{th}$ Avenue
   Denver, Colo. 80220
   This test was developed by Harvey A. Skinner, Ph.D. and was based on Selzer's MAST. The DAST is a 20-item questionnaire designed to demonstrate whether a drug problem exists as well as to demonstrate severity in a linear fashion.
4. Mortimer-Filkins Questionnaire (MFT).
   National Technical Information Service
   U.S. Department of Commerce
   5285 Port Royal Road
   Springfield, Va. 22151
     Specify: U.S. Dept. Of Transportation Pub. No. DOT-145-800, PB 209 959.
   The Mortimer-Filkins Test For Identifying Problem-Drinking Drivers was co-created by Rudolph G. Mortimer, Ph.D. and Lyle D. Filkins and includes a 58-item questionnaire designed to differentiate problem from non-problem social drinkers. Designed to evaluate drinking-drivers referred by the courts, the questionnaire should be accompanied by the Mortimer-Filkins Interview component for maximum validity. The Mortimer-Filkins test was designed to be used along with other types of information relevant to making a diagnosis, such as blood alcohol concentration (BAC) at time of arrest, driving record, criminal history, and other data usually available in court proceedings.
5. The Substance Abuse Subtle Screening Inventory (SASSI)
   The SASSI Institute
   P.O. Box 5069
   Bloomington, Ind. 47407
   A 93-item questionnaire designed to distinguish between substance dependent and non-dependent people. It has been asserted that individuals are not likely to feel threatened by the questions, and persons who try to conceal their problems will have difficulty guessing how to answer.

Heretofore, each of the instruments designed to screen for the AOD disorder, i.e., methods created to identify the presence or absence of addictive disorders, have had their own idiosyncratic prejudices and methodological inadequacies that compromise their strengths. What has been needed in the field is a method that overcomes these inadequacies by applying the results of multiple validated screening instruments in addition to other significant informational indices, to the diagnostic process.

SUMMARY OF THE INVENTION

The present invention relates to a method of evaluating a subject's relationship with mood altering chemicals. It involves several steps, including an a evaluation of a subject's prior arrest record, if any, and assigning a weighted value thereto. Also, the invention includes an evaluation of the negative symptomatology related to the subject's developed tolerance levels to mood altering chemicals, if any, and assigning a weighted numerical value thereto. In addition, the invention includes an evaluation of potential biogenetic predisposition factors, if any, and assigning a weighted numerical value thereto.

The method of the present invention also includes a step of evaluating the subject's prior and current chemical use history and weighting any generated negative symptomatology related to the subject's medical, psychological, social and spiritual profile towards assigning the final diagnostic assessment finding. A diagnostic assessment finding is assigned to the subject based on a quantification of all the foregoing weighted values.

Ultimately, the final diagnostic assessment assignment falls within the "Chemical Use/Misuse Continuum (CUMC) Diagnostic System" as described herein, and the placement score is selected from within one of six levels that correspond to increasing risk to self or society.

DETAILED DESCRIPTION OF THE INVENTION

The present invention relates to a method that incorporates screening instrument results and adds to them additional and diverse inputs from various clinical sources. This method is referred to herein as the "Chemical Use/Misuse Continuum (CUMC) Diagnostic System" or "CUMC system". This invention overcomes the non-specific terminology problems of the DSM-IV, but is consistent with its spirit. Perhaps most distinctively, a new quantitative system of classification with operationally defined subcategories has been created that recognizes and identifies subclassifications both within the chemically dependent and non-chemically dependent populations it assesses. This new system is designed to protect public and personal safety by maximizing the probability that subjects, particularly criminal justice system offenders, receive optimal diagnostic assessments in order that their education/counseling/treatment needs are safely met, without overwhelming them with unnecessary and costly counseling excesses.

In practicing the methods of the present invention, an assessment of the individual patient or subject is made on a continuum from abstinence to late stage addictive disorder. A subject's responses on a battery of assessment/screening instruments combined with documented prior alcohol/drug mediated offenses and a thorough but focused biopsychosocial interview provide the pool of information from which a quantification of negative symptomatology, is made. Both the number and severity of signs and symptoms are assessed. Through a series of decision trees individual symptoms are weighted and totaled to determine appropriate placement within one of the six primary levels that make up the Continuum of Chemical Use/Misuse. The process was created as a criminal justice model but is adaptable to other chemical misusing populations.

The present invention is a diagnostic method referred to as THE CHEMICAL USE/MISUSE CONTINUUM (CUMC) DIAGNOSTIC SYSTEM, an in-depth substance abuse/use assessment process. In addition to its capacity to identify the presence or absence of substance dependence, substance abuse or non-problematic substanceuse, the CUMC Diagnostic System measures the degree of the dysfunctional chemical use relationship.

This model was originally developed for criminal justice settings and presupposes that some type of chemically mediated dysfunctional behavioral outcome or consequence has occurred which has resulted in a client seeking an assessment and counseling services. Therefore, some degree of dysfunction is presupposed. The assessment task is to measure the severity of that dysfunction. If the client is 'chemically dependent', the degree of the chemical dependency severity is determined. If the assessment finding is in the non-chemical dependency range the degree of non-chemically dependent misuse is determined. This model is committed to promoting public safety first. However, it is also profoundly client centered in that it indicates multiple counseling options/levels that can be adapted to the client's individualized chemical education/counseling needs, as identified by the CUMC Diagnostic System.

The following sections will describe:
1. The methodology that underlies the assessment process and the six levels of increasing dysfunction, that make up the CUMC.
2. An addiction disorder model that defines the nature of chemical dependency.
3. The attributes of the model with respect to its;
   a. user friendliness and time efficiency for both staff and clients.
   b. cost effectiveness,
   c. drastic reduction of the non-specific terminology that is characteristic of the American Psychiatric Association's Diagnostic Statistical Manual-IV (DSM-IV), substance disorder definitions
   d. superior clinical consistency,
   e. superior clinical integrity,
   f. ability to categorize severity, into multiple non-chemically dependent and separately, into multiple chemically dependent sub-ranges,
   g. sensitivity to both community safety and to the clients' right to not be overwhelmed with unnecessary counseling sanctions
4. A summary discussion describing the task of the CUMC Diagnostic System.
5. A mock client walkthrough assessment
   a. Client greeting and paperwork packet assignment
   b. The counselor invites the client into their office and completes the client orientation to the assessment process and conducts biopsychosocial interview.
   c. Utilization of the Staffing Recommendation Worksheet to determine final staffing assessment level and counseling recommendation.

I. Underlying Methodology of the Invention

Involvement in the criminal justice system with the task of assessing chemical use/misuse and recommending appropriate levels of alc/drug counseling carries with it a huge responsibility, both to clients and to the community. Therefore, the mission of this method is oriented to the client and to the community. To the client the intent is to recommend a level of counseling that should safely meet the client's needs to avoid future alcohol and other drug (AOD) related problems, while protecting the client from unnecessary counseling sanctions. For the community the intent is to recommend a level of counseling that will minimize the risk of future community threatening AOD mediated client behaviors. These 'community threatening AOD mediated client behaviors', include more than recidivism or rearrest outcomes! Any chemically mediated threatening or irrational behavior(s), such as verbal, emotional, or physical forms of violence, or other behaviors that result in creating additional significant stressors such as financial, social, medical etc., for the individual or family, each, negatively impact the community as well, regardless if it fails to result in an arrest.

Professional assessment counselors, seek to balance these 'client and community oriented interests' in all of their counseling recommendations. However, the CUMC model is designed to accommodate the Criminal Justice System. Therefore, another underlying principle of the staffing criteria philosophy is, that if counselors are to err in the assessment it should be on the side of public safety, and at the risk of having to engage the client in a counseling/treatment recommendation that may nominally overshoot his/her counseling needs.

The Chemical Use/Misuse Continuum (CUMC), with its six levels of increasing dysfunction (see attachment A), includes all points across the spectrum of chemical use. It is designed for those clients who engage in any amount of alc/drug use or have a history of chemical misuse. The first three levels, with its sub-levels, encompass the non-chemically dependent range and include the DSM-IV's 'substance abuser' category. Levels four through six are sub levels of the chemically dependent range and are consistent with the DSM-IV criteria for 'substance dependence', but each has increasingly more severe symptomatology.

Clinical experience teaches that the combination of the stigma attached to chemical problems and the basic dislike of being labeled as a problem, alcoholic, or a chemically dependent user often results in highly elevated resentment levels in the client. This enduring resentment tends to sabotage any attempts towards motivating the client to consider and perhaps accept the need for positive behavioral change. Therefore, these six levels should be presented to him/her, as a Risk of Reoffending Continuum, in which 'Reoffending', is defined as, community threatening alcohol and other drug (AOD) mediated client behaviors (including but not limited to rearrest). The more substantial the problem, the greater the risk that without counseling and/or positive behavioral change, the problem will recur.

When the counselor visits with the client to explain the final staffing recommendation results, it becomes much less threatening and considerably easier for the client to accept a diagnostic result that is presented in the form of a risk of reengaging in negative behaviors, rather than in,the form that may include stigmatized labels such as 'problem user', 'abuser', 'chemically dependent', or 'alcoholic'.

This allows the complete avoidance of 'labeling'. As proper rapport is established the assessment interaction should focus on sharing and explaining the signs and symptoms that may suggest an unhealthy relationship between the client and their chemical(s) of choice, i.e. "it is because of these 'red flags', whether they be blackouts, family history, prior chemically mediated offenses, excessive chemical indulgence, etc., that place one farther down the continuum."

When the level placement is presented in this manner, the counselor focus is solely on the criteria/specific symptoms that resulted in that finding. The counselor then counsels with the client on those important concerns. Additionally, the assessment counselor should compare the counseling recommendation finding with the more substantial recommendations that are attached to the higher level findings on the continuum. This allows the client to see that, relatively speaking, there are plenty of more serious sanctions that have been avoided.

Therefore, the six levels of chemical use/misuse along the CUMC can be presented to the client and his/her attorney as parallel and increasing levels of harm risk to self and to the community which occur if the client does not undergo appropriate levels of abstinence based chemical counseling intervention. These levels, whose boundaries are demarcated by increasing numbers and/or severity of specific signs and symptoms (red flags), are as follows:

Level 1 no significant signs or symptoms outside of pending offense with the least risk to self and to public safety (i.e. non-chemically dependent—no problem range).

Level 2 (a) significant(s) sign or symptom(s) outside of pending offense with a greater risk to self and to public safety (i.e. non-chemically dependent—potential problem range).

Level 3 elevated number and/or severity of significant signs or symptoms outside of pending offense with a significant risk to self and to public safety (i.e. non-chemically dependent—problem range).

Level 4 suggestive of addictive disorder with substantial risk to self and to public safety (i.e. family and community). (i.e. problem range, with symptoms congruent with early stage chemical dependency severity).

Level 5 highly suggestive of addictive disorder with the probability of reoffending and/or otherwise endangering self and public safety (i.e. problem range, with symptoms congruent with moderately advanced chemical dependency severity).

Level 6 clearly an addictive disorder with the overwhelming probability of reoffending and/or otherwise endangering self and public safety (i.e. problem range, with symptoms congruent with chronically advanced chemical dependency severity).

II. A Chemical Misuse and Addiction Disorder Model, Which Appreciates the Behaviorally Symptomatic and Multifactorial Nature of the Disorder Before chemical use dysfunction can be measured, it must be defined. Dysfunctional chemical use and addictive disorders manifest themselves in behavioral symptoms. Individual propensities to develop different degrees of chemically mediated disbehaviorism are the result of multiple interacting factors. These factors include, on the one hand, individual characteristics of the person, i.e., his/her individual biochemistry, unique psychology and the environment in which he/she has experienced life, including its levels of stressors and cultural cues, that help to create the milieu in which he/she lives. These factors interact in an idiosyncratic way with the pharmacological characteristics specific to the drug(s) of choice, such as its unique reinforcing properties, its route of administration, and its intensity of use.

By definition, if there are no significant negative behavioral outcomes from one's use of chemicals then there is no dysfunction. On the other hand, the greater the chemical use dysfunction, the greater the severity and/or number of biopsycho-social-spiritual behavioral symptoms. This addiction disorder model recognizes that, generally speaking, there is no single criterion that defines the disorder, but rather a cluster or constellation of symptoms that manifest themselves, in a broad range of disturbed patterns. However, what is consistent throughout all of its manifestations are core indicators of addictive disorders including, compulsion/preoccupation, impaired control and continued use despite the known threat of adverse (self-injurious) consequences. Potential signs and symptoms are defined and grouped under the several categories of negative symptomatology that describe the disorder.

These categories include and capture indicators related to:
Compulsion
Physical dependence
Impaired control
Continued use despite known adverse consequences
Inappropriate use
Predisposition Any negative symptomatology is gleaned from three primary sources that are investigated in the information-gathering stage of the assessment process. These three informational sub pools are:
1. Prior record,
2. A battery of screening instruments, and
3. A bio-psycho-social-spiritual interview (referred to as chrono criteria, which additionally explores qualifying responses in any of the other informational sub pools).

The assessment process seeks to quantify the number and severity of these symptoms in order to approximate and appropriately identify where on the chemical use/misuse continuum the client resides. Once this has been determined, specific counseling options congruent to this placement are recommended.

III. The Combination of Attributes of the CUMC Diagnostic System, That Makes it Useful for a Criminal Justice Assessment and Counseling Recommendation Process Criminal justice assessment processes reviewed to date have had poor discriminating capacities resulting in an inadequate number of potential counseling recommendation outcomes. As a result, large numbers of clients are herded into programs in which they may be "set up to fail" due to, among other things, the disparate counseling/education needs of the clients accessing the identical program level. For instance, in the state of Texas, a first time DWI offender is often required to attend the stand alone 12 hour DWI class sanctioned by TCADA, even though many offenders may have more problematic relations with drinking (Mortimer-Filkins claims as high as 50% of these first time DWI offenders are problem range drinkers). Meanwhile a subsequent offense with conviction results in assignment to the DWI Repeat Offender program, with more serious offenders being referred to Intensive out or in-patient treatment, only after multiple offenses. Placement into one of these three or four counseling levels are based many times on ill defined considerations of prior record information, combined with only one or two screening instrument results and blood alcohol concentration results. Inadequate informational inputs combined with the absence of clear decision rules cripple any chance of generating assessment findings that are consistent and have predictive value.

By contrast, The CUMC Diagnostic System is an assessment process that includes decision rules based on a comprehensive system of diverse and multiple informational inputs. These inputs acknowledge and are necessary to monitor the complex/multidimensional interacting co-factors that cumulatively result in an individual's susceptibility to developing dysfunctional relationships with mood altering chemicals. At the same time, the system identifies the presence and severity of signs and symptoms that arise during the maturation process of chemical misuse disorders. This dynamic property of the system also allows it to distinguish and define its lower levels, that is, the three non-chemically dependent relationships one may have with his/her chemicals of choice.

The three primary informational sources alluded to above, that make up the 'multiple informational inputs' include, prior record, a battery of screening instruments, and chrono criteria results. These sub pools combine to form the final pool of informational inputs (data elements). A decision tree complex then yields a final staffing outcome.

The unique package of advantages of the CUMC and staffing guidelines are reflected by the combination of the following attributes:

1. It is user friendly and time efficient for both staff and clients.

Once the scoring of the instruments, and interview process is complete (30–45 counselor min.), a trained staff member can complete the decision process within three to ten minutes, depending upon experience using the process.

2. It has superior clinical consistency

When the decision rules are followed correctly, the system is inherently consistent in its initial assessment results. Thus, it maximizes consistency in staffing outcomes throughout the agency regardless of the differences in chemical dependency counseling and/or assessment experience of the participating assessors.

3. It has superior clinical integrity

It is consistent with DSM-IV definitions and guidelines for the proper diagnosis of chemical dependency, and It is superior to the DSM-IV, with regard to its mission to assess the degree or severity of chemical problems, in that it:
   a. drastically reduces the non-specific terminology that plagues the DSM-IV definitions, as well as,
   b. allows for specific operationally defined sub levels of severity both within the non-chemically dependent range and within the chemically dependent range.

It ensures the integrity of proper approximation placements on the CUMC, by integrating an understanding of the multi factorial and multi dimensional nature of chemical problems within its decision rule process.

It provides multiple decision trees which are then accessed by the potentially diverse symptomatic inputs (data elements), collected in the information gathering portion of the assessment process, reflecting its appreciation of the multifactorial nature of the disorder. These data elements represent all the diverse elements of the information pool generated from integrating the battery of assessment instrument results, the prior record, and a thorough exploration of relevant biopsychosocial informational history (see Bio-psycho-social—spiritual Investigation Summary).

It acknowledges that many different combinations in which symptoms can be manifested that generate individualized client profiles can reside at the same point along the continuum.

In other words, this model recognizes that this disorder, at all levels along the continuum, expresses itself differently in different people. Therefore, although two clients may reside at the same point along the continuum there is an appreciation that there are often different symptomatological combinations that resulted in this placement.

4. The system measures severity of dysfunction independent of the presence or absence of chemical dependency.

For those clients assessed as Non-Chemically Dependent (NCD), there are two non-problem levels (Levels 1 & 2), and one problem but NCD level (Level 3—composed of six sub level ranges), each reflecting increasing dysfunction.

For those clients assessed as most likely Chemically Dependent (CD), there are three levels (Levels 4–6), with the most chronically advanced severity level (Level 6), having multiple sub level ranges.

5. It is cost effective

With the exception of the SASSI, the preferred screening instruments are in the public domain.

6. It is community and client oriented

Members of the community, who like all of us are potential clients, deserve to have a criminal justice system that provides in-depth and competent diagnostic assessments. It does not take a doctor to appreciate that in order to efficiently and successfully treat any type of health disorder, an accurate assessment of the severity of the presenting problem is required.

IV. Summary Discussion Describing the Task of the CUMC Diagnostic System 1. appreciating and capturing the constellation of biogenetic, psychological and social co-factors that interact to form the individual susceptibility of developing chemical misuse problems, and
2. through this assessment model, identifying and quantifying the number and severity of negative symptoms and markers related to chemical misuse.

Addictive disorders defy exact diagnosis with respect to precise time of onset and vary from host to host. There is a confluence of factors, at varying intensities, that converge and manifest themselves in each host, as a unique expression of the disorder. These many factors express their presence or absence through the presence or absence of symptoms or markers. If they are present, then the model seeks to measure their number and severity. Importantly, it is through the psychosocial interview process that these symptoms and markers are explored for presence and severity. Once all these symptoms and markers are aggregated a final placement along the Chemical Use/Misuse Continuum is generated as the final assessment result. It is precisely this task that this multiple decision tree process embodies.

Through a multiple decision tree process the following markers and disbehavioral chemically mediated symptomatology is quantified.

1. Prior chemically mediated arrest record, including blood alcohol concentration (BAC) results
2. Chemically mediated social, work, health, or family related problems
3. Chemical use patterns, with respect to frequency and quantity
4. Family history of addictive disorders,
5. Blackouts This decision tree complex includes 11 trees and the following inputs:

a. Four decision trees that input screening tool results, including the:

Michigan Alcohol Screening Test (MAST), Numerical Drinking Profile (NDP), Substance Abuse Subtle Screening Inventory (SASSI), and depending upon type of arrest, the Mortimer-Filkins Test for Identifying Problem Drinking Drivers (MFT), or the Drug Abuse Screening Test (DAST).

b. Four decision trees that input chrono criteria

Criteria specific to the presence and degree of family history of addiction

The presence, frequency and degree of blackouts,

Blood alcohol concentration (BAC), at time of arrest, as well as BAC with respect to weekly drinking patterns, and Chemical use patterns with respect to quantity, frequency, and mode of administration.

c. One decision tree ('Other Significant Chrono Criteria Elements') that allows for 'other chrono criteria' reflecting additional red flags not considered in the above (b) decision trees.

1. Prior counseling modalities
2. Impaired control
3. Continued use despite known substantial risk or adverse consequences
4. Other significant drug use d. Two decision trees that input staffing criteria related to prior record Four of these decision trees have combination properties that include input from several decision trees before their outcome can be determined. This allows for the appreciation of the negative synergistic symptomatology that different combinations of signs and symptoms often manifest and which place clients at a higher risk of reoffending. For example, the same screening instrument scores when combined with additional red flags warranting special attention (such as, but not limited to, a chemically mediated prior record or significant family history of addictive disorders), yield a higher assessment finding.

V. Mock Client Walkthrough

A. Client Greeting and Paperwork Packet Assignment.

When a client shows up for an appointment he is greeted by the receptionist and is given a folder of paperwork to review and begin filling out. This packet includes:

1. An information/instruction sheet that outlines the assessment process for the client with assurances that an assessment counselor will be personally interview the client and be available to answer any questions, once the paperwork has been completed.
2. A personal data sheet that records general client demographic information, with a prefilled box in the upper right hand corner, identifying the referring information (type of referring offense, referral agency, court setting information, case cause number, attorney/probation officer of record, etc.)
3. The battery of screening instruments depending upon the type of referral will include the MFT or the DAST, along with the MAST, NDP, and the SASSI.
4. Client's rights, grievance process, and rules of conduct.

Clients are prescreened for reading ability. Upon completing all the forms included under 1–3 above, which depending on reading ability generally averages 15–30 minutes, they are instructed to return folder to front desk. There the paperwork is reviewed to assure that all important items are completed. A counselor is summoned to begin scoring the screening instruments and reviewing the paperwork while the client finishes reading the Client's rights, grievance process, and rules of conduct. This review process generally averages 10 minutes or less. Once this process is completed the client is invited into the assessment counselor's office to complete the psychosocial component of the assessment process B. The Counselor Invites the Client Into Their Office to Complete the Client Orientation to the Assessment Process and to Begin and Complete the Biopsychosocial Interview.

The counselor describes the intent of the assessment process and the non-punitive nature of the office and counseling function. The counselor responds to any questions the client may have as he/she attempts to develop some rapport.

The psychosocial interview is a process protocol that is designed to explore, clarify, and pinpoint all identified qualifying informational criteria that impacts the outcome of any of the decision trees outlined below. These criteria include both relevant screening instrument responses as well as other 'chrono criteria' reviewed following the psychosocial interview process form. Depending upon the severity of the finding and resentment levels of the client, this interview portion of the process should average 20–40 minutes.

C. The Bio-psycho-social-spiritual History Process

In addition to identifying client strengths, weaknesses and needs, the purpose of the psychosocial interview is to provide an in-depth historical and current descriptive exploration/analysis of:

1. all significant signs and symptoms of, or markers for, potential or evident problem chemical misuse (i.e. red flags), and
2. any important mitigating circumstances, that may have influenced the evolution of the potential or evident chemical misuse problem, and/or may need to be addressed if they pose significant roadblocks to effecting desired behavioral change.

These red flags are the building blocks that provide the clinical foundation for the diagnostic assessment findings that are conveyed through the Screening Reports (SRs). Therefore the integrity of the information specific to establishing the existence of the symptom as well as the extent of its severity or parameters is essential to the process and cannot be compromised. These red flags must be clearly explored and translated into a written communication in the psychosocial report. They will provide the necessary informational insights needed to enter those findings into the decision tree apparatus, that is largely. responsible for generating our final assessment level finding. A "Bio-Psycho-Social-Investigation Summary" document is presented as Model 1 below:

MODEL FORM 1. Bio-psychiosocial-spiritual Investigation Summary (with Exploration Criteria Guidelines)

Education and Employment (The psycho-social investigation begins with the sections on education/employment and then family/dependents. These are non-threatening domains. Thus, rapport building can be initiated before probing more sensitive areas. A review of the personal data sheet content should occur before exploring these areas. Begin with present employment status and explore work history. Depending on age, the last 10 years of work history or last four jobs whichever can be garnered more quickly.)

Family and Dependents (Review personal data sheet before exploring this area. Living situation is explored. With whom does the client live, are there dependents, are finances stable, will the living environment supportive of an abstinence oriented life style commitment decision if in fact the client chooses one, etc.)

Medical (Current medical status and past significant health problems are noted. Does client have health insurance carrier, if so, its name. If client is presently taking any prescribed medications or has a history of prolonged prescription drug use, explore and describe. Explore and notate if client knowingly threatened his/her health by continued drinking despite doctor's contrary advice.)

Psychiatric (Explore if client is presently or in the past sought help for a psychiatric/emotional problem, if so what type and duration of help was received, i.e. drug therapy, psychotherapy, institutionalization etc.)

Prior Arrest Information (Arrest history, including type, date, final disposition, whether any alcohol or other drugs were consumed or possessed the date of the alleged offense, the results of any breath or blood test that may have been given. Note: As you broach the subject, always assume that any prior offenses occurred after drinking. By asking if client had been drinking before the arrest, many clients may identify the incriminating importance of such information. For the purposes of making accurate assessments, ask instead if they were intoxicated/drunk during the offense, or did they just have 'a few beers' . . . implying it was the circumstance and not the chemical use that was responsible for the offense.)

Client's Version of Current Arrest (This is another opportunity to build rapport by allowing the client to describe from his own perspective, the circumstances surrounding the arrest. However, in the interests of saving time, the counselor should lead and move the client through this discussion by asking, where, how many, what type, over what time period, taking any other medications, what client behavior brought him/her to the attention of the arresting officer? Did client feel intoxicated or that they were driving badly/unsafely?)

Drinking Pattern

Client weight =____lbs.
Drinks____x wkly/mnthly/yrly
Average # of drinks per sitting =____
Avg. time period of consumption =____hrs
Average BAC wkly =____(i.e. DPQ)

(This is another area where the counselor can minimize the time requirements. An interviewer should lead the client through this section by asking the following direct questions and politely, but firmly, refocus clients if they stray from the informational intent necessary for our staffing needs.)

1. What type of drink is preferred, mixed drinks, beer, or wine.
2. What is the frequency, how many days per week, or if not weekly per month does client drink. Note: Many clients will resist being pinned down, indicating they may not drink on a set schedule. In that case a patient validation, such as, "we realize you do not drink the exact same number of times each week, but on the average what would that look like?" should be pursued.
3. Regarding quantity, on those occasions client does drink, how many drinks over how many hours. Note: The staffing criteria gives significant weight to tolerance issues based on regular drinking patterns (defined as at least 1×wkly); therefore, the importance of establishing the presence or absence of a weekly pattern of consumption. Significantly less staffing weight is given to the same estimated blood alcohol level when it is realized on less than a once a week basis.

Be sure to always establish current use patterns, first. Then move on and explore first use, first intoxication [defined as 5 or more drinks in one setting], if there were past periods of abstinence or more heavy or problematic drinking patterns, etc.)

Other Drug Use Pattern (Be sure to always establish current use patterns firsts, including drug types, how often, how much, etc. Then move on and explore first use, first regular use [defined as 1×a month or more often], if their were past periods of abstinence or more heavy or problematic drugging use patterns, etc. Route of administration is of particular importance.)

Prior Treatment and/or Counseling (Include dates, level of care, length of care, successful or unsuccessful discharge, involvement history in both aftercare and 12-step support groups. Length of recovery and/or abstinence. Note: It is the responsibility of the evaluating counselor to ensure the client has not been through counseling programming before. All attempts to procure old file should be made before final staffing.)

_____-(End of Model Form 1)-_____

Screening Instruments & Chrono Criteria

Explore screening instrument qualifying responses, and ensure exact determinations of those chrono elements that make up the chrono criteria decision tree (BAC, DPF, DPQ, FH, & blackouts) have been adequately covered.

I. Drinking Patterns with Respect to Quantity (DPQ) and Frequency (DPF)

II. Blood Alcohol Concentration (BAC)

The blood alcohol concentration level at the time of arrest is an important staffing element and therefore has its own specific decision tree. However, it is only a snapshot in time. Unless it is chronically elevated, as a stand alone staffing element it does not provide a clear insight as to the degree of developed tolerance nor establish a pattern of abuse. However, it is extremely important for its collaborative potential. Previous BAC results from prior arrests should also be explored.

III. Family History of Addictive Disorders (FH)

Due to the significance of this marker it also has its own specific decision tree. Always confirm its absence, and in its presence, confirm its extensiveness, with respect to number of identified family members, severity of their addictions, and specific relationship to the client. Regarding confirmation of this marker, a brief note indicating the most obvious symptoms of the relative's addictive disorder should be explored and documented in writing, i.e. 'he has had multiple DWIs', or 'he/she has been in Intensive out-patient treatment before', etc.

Often clients may deny any family history of alcoholism, however on question #38 on the Mortimer Filkins Test indicate an excessive drinker in their family. When asked to describe what about their drinking makes it excessive in their eyes, their description may describe substance dependence. Direct family history includes siblings, parents, and grandparents. See 'Family History of Addictive Disorders Chart', below for scoring parameters.

Chronic family history is defined as a family history score of two or more. The closer the blood lineage the more weight is given. The indirect lineage column can never exceed .50 for the purposes of determining a total score. This is due to the rather diluted blood lineage of cousins.

IV. Blackouts

Confirmation and then total number of blackouts and the time period over when they occurred are the necessary data elements. First blackout, frequency (are they more frequent) last occurrence should also be explored.

V. Impaired Control

Making claims of physical loss of control (impaired control) in psychosocial must be clearly explicated in writing, both with respect to describing specific examples and its frequency and confirmed with the client before we can give it the full staffing criteria weight it deserves as a major/primary clinical indicator of addictive disorders. Statements in the psychosocial such as 'occasional loss of control' or any other statements that fail to clearly define and describe the nature of the impaired control. They are considered clinical evaluation errors as they seriously compromise the validity of the criteria claim for our staffing purposes.

VI. Confirmation of Specific Non-qualifying Responses

Due to the importance of the following elements, a confirmation of the following non-qualifying responses is required. Family history of addictive disorders, blackouts and significant behavioral control loss (physical fights, acting out in a way that is substantially in conflict with one's value system, verbally offensive behavior resulting in loss of friends, i.e. Have you ever lost friends because of your drinking or drugging behavior?)

VII. Other Considerations

Generally speaking, highly elevated patterns w/respect to frequency may not be as significant a marker as the FH, blackouts, BAC at arrest, or DPQ. Many individuals drink regularly but moderately w/little or no negative consequences until their arrest. After being arrested, continued elevated patterns w/respect to frequency, but w/moderate consumption amounts, is considerably more significant, but even that could be the result of very poor judgment alone. In other words, as a stand alone red flag, (i.e. no other red flags outside of arrest), this criteria holds significantly less staffing weight than, chronic FH, chronic DPQ, or chronic BAC, all of which have their own specific decision trees. Weight adjustments have also been made within the Chrono criteria decision tree which include all these potential symptoms.

At this point in the biopsychosocial process all necessary defining characteristics related to determining the Total Chrono Criteria Score must be documented (i.e. re: DPQ, DPF, FH, BAC @ arrest, and Blackouts). A "Family History of Addictive Disorders Chart" follows as Model Form 2.

| Model Form 2. Family History of Addictive Disorders Chart | | |
|---|---|---|
| Direct blood lineage (1.0) | Less Direct blood lineage (.5) paternal/maternal | Indirect lineage (.25) |
| Father | Grandfather | Cousins |
| Mother | Grandmother | |
| Brother | Uncle | |
| Sister | Aunt | |
| Offspring | Half sibling | |
| sub-total = | sub-total = | sub-total = |
| | FH total weight score =____ | |

-continued

Model Form 2. Family History of Addictive Disorders Chart

| Chrono Criteria Scoring Chart | Description | Sub Score |
| --- | --- | --- |
| 1. Drinking patterns with respect to frequency | | |
| 2. Drinking patterns with respect to quantity (DPQ). Applicable only if client drinks at least 1 × weekly (= regular drinker) | Averages____beers/drinks over____hrs =____BAC = avg wkly BAC per sitting | |
| 3. Family history of addictive disorders | | |
| 4. Blood Alc. Concentration (BAC) @ arrest | | |
| 5. Blackouts | | |
| | Total Chrono Criteria Score = | |
| | - END OF MODEL FORM 2 - | |

Counselor's Evaluation & Criteria Highlights

Client strengths, weaknesses and needs are recorded. For the purposes of determining the degree of Chemical use/misuse severity, a list of the significant criteria that was garnered from the prior record, screening instrument results and the biopsychosocial interview is succinctly described.

Additionally, Other Significant Chono Criteria should be highlighted, including

| Other Significant Chrono Criteria Elements: | Please circle & describe |
| --- | --- |
| 1. Prior counseling modalities | applicable/non-applicable |
| 2. Impaired control | applicable/non-applicable |
| 3. Continued use despite known substantial risk or adverse consequences | applicable/non-applicable |
| 4. Other significant drug use | applicable/non-applicable |

[See Decision Tree #12 for detailed description of each element 1–4.]

Before the counselor writes up their own recommendation the Staffing Recommendation Worksheet should be completed. State the outcome of the Staffing Recommendation Worksheet assessment level finding.

General Considerations:

Staffing criteria with the most weight should be given special attention to detail in the biopsychosocial exploration. Criteria given the most weight in the CUMC can be determined by:

does it have its own decision tree and by itself place someone into level 4?

can it along w/another criteria place someone into a level 4 (i.e. is it included in a combination chart?)

In this way it is evident that the most powerful decision trees include:

1 (prior record), #2 (MAST), #3 (chrono criteria), #6 (PR Combination Chart), #9 (DAST), #11 (BAC), and #12 ('other').

The next most powerful decision trees would include:

4 (FH), #5 (DPQ) and #11 (SASSI)

The least powerful decision trees would include:

8 (NDP) and #10 (MFT) trees

Concluding remarks to ' . . . client orientation to the assessment process and completion of the biopsychosocial interview.'

It is the job of the assessment counselor, then, to identify data elements that need further clarification and explore and explicate them, in a timely manner. Client waiting time must be minimized while, attaining the necessary detail required by the assessment/psychosocial investigation criteria guidelines.

Upon completion of the Bio-psycho-social-spiritual Investigation Summary form, any additional client questions should be answered. This client should be given a ballpark estimation of the final staffing results and an understanding that the final staffing outcome is the result of other counselors input following established staffing criteria guidelines. The client should be thanked for their cooperation and be advised that the assessment recommendation shall be formalized and be available to them and/or their attorney before the final disposition date. The client is also advised to stay in touch with the court and his/her attorney to ensure being present at all necessary court appearance dates.

Before the counselor writes up their own counselor recommendation the Staffing Recommendation Worksheet is completed and its outcome is reflected under the 'Counselor's Evaluation and Criteria Highlights' section of the Bio-psycho-social-spiritual Investigation Summary.

D. Summary Conclusion and Utilization of the Staffing Recommendation Worksheet to Determine Final Staffing Assessment Level and Counseling Recommendation.

Upon conclusion of the biopsychosocial interview the final pool of clinically relevant data elements (signs/symptoms and/or markers) has been established. These data elements include criteria related to:

Prior record results

Multiple screening instrument results

Biopsychosocial interview results

From these sub-pools, information specific to negative symptomatology related to the following areas, are quantified and qualified through a system of 12 decision trees. Areas include:

Prior record

Screening instrument scores and qualifying responses from the:

MAST, SASSI, DAST/MFT, and NDP

Tolerance (DPQ)

Drinking/drugging patterns with respect to frequency, quantity and mode of administration Blood alcohol concentration (BAC) at arrest Blackouts Family history of addictive disorders Prior counseling modalities Impaired control Continued use despite known substantial risk or adverse consequences Importantly, there is a clinical override decision tree (#12) that allows for the overriding of the result of the decision tree 1–11 outcome, if integrible clinical factors are uncovered outside the domain of the first 11 decision trees.

The muultifactorial nature of substance use disorders as a complex interactive result of biogenetic, environmental, psychological, sociological and spiritual co-factors is appreciated. The theoretical quest to capture the multitude of forms it can present itself in its different hosts as unique expressions/constellations of its negative symptomatology, is organized and driven by a decision tree complex. This decision tree complex and the decision rules that govern its operation is The CUMC Diagnostic System. It is consistent with the rich history of addictive study outcomes and is based on the ongoing development of insights and scientific based data available in the field today. Refinements based on improvements and scientific breakthroughs will continue to be made on an annual or more frequent basis, as warranted.

E. A Client Assessment Result Profile (Model Form No. 3 Follows):

| Model Form 3. Client Assessment Result Profile | | | |
|---|---|---|---|
| Client: | John Doe | Weight: | 160 lbs |
| Pending charge: | Driving While Intoxicated (DWI) | | |
| Prior record: | Public Intoxication. - 1996 | (see 3b on Prior Record decision tree) | |
| Screening Instrument Scores: | | | |
| | MAST: | 6 | (see 3b on MAST decision tree) |
| | SASSI: | NCD | |
| | MFT: | Q-17 | |
| | NDP: | 2 | |

| Criteria Profile Scoring Sheet Summary | | |
|---|---|---|
| Chrono Criteria I Score Components | Description | Sub score |
| 1. Drinking patterns with respect to frequency of use per wk | 3 × weekly | 2 |
| 2. (weekly) Drinking Patterns with respect to Quantity (DPQ) per sitting = Average BAC per sitting each wk | Client wt = 160 lbs. Avgs 5 beers or drinks over 2 hrs = .07 BAC per sitting | 2 |
| 3. Family history of addictive disorders (# and blood lineage relationship) | Brother | 2 |
| 4. Blood Alc. Concentration (BAC) @ arrest | .18 BAC | 3 |
| 5. History of Blackouts | 1 blackout 2 yrs ago | 2 |
| | Total Criteria Profile Score = | 11 |

Other Significant Chrono Criteria Elements:
1. Prior counseling modalities—none
2. Impaired control—n/a
3. Continued use despite known substantial risk or adverse consequences—n/a
4. Other significant drug use—n/a 2. maximize consistency in staffing outcomes throughout our agency.

This worksheet has multiple staffing element decision trees, several that can be eliminated based on the specific client pr. Each of the decision trees that remain generates specific minimum findings. Whichever finding is the farthest along the Chemical Use/Misuse Continuum represents the preliminary appropriate staffing recommendation. Formal staffing follows with other counseling team members, one of which must be an LCDC, and includes discussion of any other important data and dialogue; culminating in the final

| STAFFING RECOMMENDATION WORKSHEET Client Name/DOB: John Doe/Dec. 6, 1965 | | |
|---|---|---|
| Staffing Element | Decision Tree | minimum recommendation and/or assessment level = |
| 1. Is there a prior record (PR) → | if yes, go to PR Decision Tree → | adv. - 3 |
| 2. Is MAST score 4 or more → | if yes, go to MAST Decision Tree → | adv. - 3 |
| 3. Is chrono criteria score 2 or more → | if yes, go to CC Decision Tree → | din aa × 2 for 1 yr - 3 |
| 4. Is FH chronic → | if yes, go to FH Decision Tree → | n/a 1 |
| 5. Is DPQ chronic → | if yes, go to DPQ Decision Tree → | n/a 1 |
| 6. Is there a prior record → | if yes, go to PR Combination Chart → | IOP aa × 2-2 yr - 4 |
| 7. Is SASSI score Abuser or CD → | if yes, go to SASSI Decision Tree → | n/a 1 |
| 8. Is NDP score 3–7 → | if yes, go to NDP Decision Tree → | int. grps - 2 |
| 9. Is DAST score 3 or more → | if yes, go to DAST Decision Tree → | n/a 1 |
| 10. Is MFT score 12 or more → | if yes, go to MFT Decision Tree → | adv. grps - 3 |
| 11. Is BAC .15 or higher → | if yes, go to BAC Decision Tree → | int. grps - 2 |
| Indicate or circle highest assessment level (AL) and highest recommended counseling as determined by decision trees 1–11 above. | | |
| 12. Other Significant Chrono Criteria Elements - indicating more substantial rec. and/or assessment level finding | → | n/a 1 |

Final Staffing Assessment Level = 4 (1–6)
Recommendation = TCADA licensed Level II Intensive Outpatient Treatment and AA × 2 for two years (see continuum of recommended counseling options included under, 1. PR DECISION TREE, below)

The purpose of the staffing criteria guidelines is to:

1. make appropriate and integrible recommendations in a timely fashion, and level finding (1–6) and staffing recommendation. Following these guidelines and using this worksheet shall yield a minimum recommendation and/or minimum level finding (1–6).

| STAFFING RECOMMENDATION WORKSHEET |
| --- |
| Client Name/DOB: |

| Staffing Element | Decision Tree | minimum recommendation and/or assessment level = |
| --- | --- | --- |
| 1. Is there a prior record (PR) → | if yes, go to PR Decision Tree → | |
| 2. Is MAST score 4 or more → | if yes, go to MAST Decision Tree → | |
| 3. Is chrono criteria score 2 or more → | if yes, go to CC Decision Tree → | |
| 4. Is FH chronic → | if yes, go to FH Decision Tree → | |
| 5. Is DPQ chronic → | if yes, go to DPQ Decision Tree → | |
| 6. Is there a prior record → | if yes, go to PR Combination Chart → | |
| 7. Is SASSI score Abuser or CD → | if yes, go to SASSI Decision Tree → | |
| 8. Is NDP score 3–7 → | if yes, go to NDP Decision Tree → | |
| 9. Is DAST score 3 or more → | if yes, go to DAST Decision Tree → | |
| 10. Is MFT score 12 or more → | if yes, go to MFT Decision Tree → | |
| 11. Is BAC .15 or higher → | if yes, go to BAC Decision Tree → | |
| Indicate or circle minimum assessment level (AL) and min. recommended counseling as determined by decision trees 1–11 above. | | |
| 12. Other Significant Chrono Criteria Elements - indicating more substantial rec. and/or assessment level finding | → | |

Final Staffing Assessment Level = ____ (1–6)
Recommendation = (see continuum of recommended counseling options under 1. PR DECISION TREE below)

The purpose of the staffing criteria guidelines is to:
3 1. make appropriate and integrible recommendations in a timely fashion, and
4 2. maximize consistency in staffing outcomes throughout our agency.

This worksheet has multiple staffing element decision trees, several that can be eliminated based on the specific client profile. Each of the decision trees that remain generates specific minimum findings. Whichever finding is the farthest along the Chemical Use/Misuse Continuum represents the preliminary appropriate staffing recommendation. Formal staffing follows with other counseling team members, one of which must be an LCDC, and includes discussion of any other important data and dialogue, culminating in the final level finding (1–6) and staffing recommendation. Following these guidelines and using this worksheet shall yield a minimum recommendation and/or minimum level finding (1–6).

| PRIOR RECORD (PR) AND MAST SCORING KEY | | | |
| --- | --- | --- | --- |
| PR Code | Prior Record Key | | MAST Score Key |
| 1 = | no prior record | 1 = | MAST score of 1–3 |
| 2a = | one non-dwi class A or B misd. alc/drug related offense more than 8 yrs ago. | 2a = | MAST score of 4* |
| 2b = | one class C misd. alc/drug related offense over 6 yrs ago. | 2b = | MAST score of 5, w/out additional qualifiers |
| 3a = | one class A or B alc. Related arrest w/in past 8 yrs. | 3a = | MAST score of 5, w/ additional qualifiers |
| 3b = | PI prior w/in past 6 yrs. | 3b = | MAST score of 6 |
| 3c = | one prior DWI arrest before Jan. 1, 1984, w/no additional qualifiers** | 3c = | MAST score of 7, w/out additional qualifiers |
| 3d | 3c w/additional qualifiers | 3d = | MAST score of 7 w/additional qualifiers |
| 3e = | one prior DWI subsequent to Jan. 1, 1984 but more than 10 yrs ago (1984–1988) w/no additional qualifiers. | 3e = | MAST score of 8 |
| 3f = | 3e w/additional qualifiers | 3f = | MAST score of 8 w/additional qualifiers |
| 3g = | one prior DWI 6–10 yrs ago | 3g = | MAST score of 9 w/out additional qualifiers |
| 3h = | two prior alc/drug related arrests, regardless of how old priors are | 4a = | MAST score of 9 w/additional qualifiers |
| 3I = | one prior felony non-DWI alc/drug related probation, deferred adj. or final conviction | 4b = | MAST score of 10–11 |
| 4a = | one prior DWI within last five yrs | 5 = | MAST score of 12–14 |
| 4b = | two prior non DWI alc related prior arrests w/in past 8 yrs | 6 = | MAST score of 15–24 |

-continued

PRIOR RECORD (PR) AND MAST SCORING KEY

| PR Code | Prior Record Key | MAST Score Key |
|---|---|---|
| 4c = | three alc. Related prior arrests regardless of how old priors are | |
| 5a = | one prior DWI subsequent to Jan. 1, 1984, with two additional prior non-DWI alc related arrests, one of which was within last 5 yrs | MAST score of 4 places client at no less than level 2 unless the four qualifying responses are questions #6, 11, 12, and 30 with no additional qualifiers. In that case, a level 1 finding is possible. |
| 5b = | felony third DWI conviction | ** "additional qualifiers" = a chrono criteria score of two or more. |
| 5c = | three prior alc related arrests, two of which were w/in last 8 yrs | |
| 5d = | three prior alc. Related arrests, one of which was in last 5 yrs | |
| 6 = | Prior records more chronic than level 5 | |

1. PRIOR RECORD (PR) DECISION TREE

With pending class A or B misdemeanor DWI arrest* and a prior record of (a) places client at no less than assessment level (b), and indicates recommended counseling options include (c).

| if a = | then b = assessment level | then c = prior record clinical recommended counseling option(s) include: |
|---|---|---|
| 1. no prior record | level 1 | dwi classes only, or intermediate groups only, or drug classes only |
| 2a) one non-dwi class A or B misd. alc/drug related offense more than 8 yrs ago. or | level 2 | intermediate program |
| 2b) one class C misd. alc/drug related offense over 6 yrs ago. | | |
| 3a) one class A or B alc. related arrest w/in past 8 yrs, or | level 3 | advanced program |
| 3b) PI prior w/in past 6 yrs | | |
| 3c) one prior DWI arrest before Jan. 1, 1984, w/no additional qualifiers** | level 3 | advanced w/AA × 2 for 3 mos |
| 3d) one prior DWI arrest w/additional qualifiers or one prior felony drug***/alc. related offense more than 14 yrs ago | level 3 | DIN or w/multiple qualifiers DIN w/AA × 2 for 6 mos |
| 3e) one prior DWI subsequent to Jan. 1, 1984 but more than 10 yrs ago (1984–1988) w/no additional qualifiers | level 3 | DIN w/AA × 2 for 6 mos |
| 3f) w/additional qualifiers | level 3 | DIN w/AA × 2 for 1 yr |
| 3g) one prior DWI 6–10 yrs ago | level 3 | DIN w/AA × 2 for 1 yr, or w/qualifiers AA × 2 for 2 yrs |
| 3h) two prior alc/drug related arrests regardless of how old priors are or | level 3 | DIN w/AA × 2 for 2 yr |
| 3i) one prior felony alc/drug related probation, deferred adj. or final conviction w/in past 14 yrs | | |
| 4a) one prior DWI within last five yrs or | level 4 | IOP & AA × 2 for 2 yrs 30/30 followed by DIN (to be completed w/in 100 days) |

-continued

| if a = | then b = assessment level | then c = prior record clinical recommended counseling option(s) include: |
|---|---|---|
| 4b) two prior non DWI alc related prior arrests w/in past 8 yrs or 4c) three alc. related prior arrests regardless of how old priors are. | | followed by AA × 2 for yrs**** 90/90 (plus Advanced in the absence of prior treatment), followed by AA × 2 for 2 yrs |
| 5a) one prior DWI subsequent to Jan. 1, 1984, with two additional prior non-DWI alc related arrests, one of which was within last 5 yrs or 5b) felony third DWI arrest or 5c) three prior alc related arrests, two of which were w/in last 8 years 5d) three prior alc. related arrests one of which was in last 5 yrs | level 5 | IOP & AA × 3 for 2 yrs IOP - DIN & AA × 3 90/90 & DIN - AA × 3 |
| 6. Prior records more chronic than level 5 | level 6 | Daily AA until IOP begins followed by AA × 4 IP/OP screening with daily AA until treatment begins followed by: a. AA × 4 b. 90/90 then AA × 3–4 c. DIN then AA × 3–4 | note: The bolded red areas represent The continuum of recommended counseling options available in Travis County TX.
note: See Table I for program description of each counseling option listed in The continuum of recommended counseling options.
note: Anywhere that IOP is recommended aftercare is assumed
*Staffing Tip - Be sure to reverse pending and prior offense, above, when pending alc. related offense is not a DWI offense, but prior is, in order to determine minimum possible assessment level.
**additional qualifier(s) allude to data elements that by themselves place client in no less than a level 2 finding (i.e. a BAC of .15–.19, PSA on the SASSI, a total score of 2–3 on chrono criteria, etc.)
***felony drug offenses with respect to mandatory length of recommended 12-step meetings, discretion is encouraged with respect to non using drug dealers.
****pretrial option only; i.e. client has not been placed on probation, and therefore client is being case managed by assessment agency, which ensures that all treatment plan requirements are followed.

2. MAST DECISION TREE

With pending class A or B misdemeanor DWI or other alc./drug related arrest and a MAST SCORE of (a) places client at no less than assessment level (b), and indicates recommended counseling options include (see 'c' above).

| if a = MAST score | then b = assessment level | then c = rec. counseling options |
|---|---|---|
| 1. MAST score 1–3 | level 1 | |
| 2a) MAST score 4* or 2b) M-5 w/out additional qualifiers | level 2 | |
| 3a) MAST score 5 w/additional qualifiers or 3b) MAST score 6 | level 3 | Advanced |
| 3c) MAST score 7 w/out additional qualifiers | level 3 | Advanced w/AA × 2 for 3 mos |
| 3d) MAST score of 7 w/additional qualifiers | level 3 | DIN |
| 3e) MAST score of 8 | level 3 | DIN w/AA × 2 for 6 mos |
| 3f) MAST score of 8 w/additional qualifiers | level 3 | DIN w/AA × 2 for 1 yr |
| 3g) MAST score of 9 w/out additional qualifiers | level 3 | DIN w/AA × 2 for 2 yrs |
| 4a) MAST score of 9 w/additional qualifiers or 4b) MAST score of 10–11 | level 4 | IOP & AA × 2 for 2 yrs 30/30 followed by DIN (to be completed w/in 100 days) followed by AA × 2 for yrs**) 90/90 (plus Advanced in the absence of prior treatment), followed by AA × 2 for 2 yrs |
| 5) MAST score of 12–14 | level 5 | |
| 6) MAST score of 15–24 | level 6 | |

*MAST score of 4 places client at no less than level 2 unless the four qualifying responses are questions # 6, 11, 12, and 30 with no additional qualifiers. In that case a level 1 finding is possible.
**pretrial option only

3. CRITERIA PROFILE DECISION TREE

| Chrono Criteria total score | Minimum Level Finding | Recommended Counseling Options |
|---|---|---|
| Score of 2–3 | level 2 | intermediate program |
| Score of 4–5 | level 3 | advanced program |
| Score of 6 | level 3 | advanced w/AA × 2 for 3 mos. |
| Score of 7 | level 3 | DIN |
| Score of 8–9 | level 3 | DIN w/AA × 2 for 6 mos. |
| Score of 10–11 | level 3 | DIN w/AA × 2 for 1 yr. |
| Score of 12 | level 3 | DIN w/AA × 2 for 2 yrs. |
| Score of 13 or more | level 4 | Note: a score of 13 could indicate a level 4, 5, or 6. |

3. CRITERIA PROFILE DECISION TREE (continued)

Family History of Addictive Disorders Chart

| Direct blood lineage (1.0) | Less Direct blood lineage (.5) paternal/maternal | Indirect lineage (.25) |
|---|---|---|
| Father | Grandfather | Cousins |
| Mother | Grandmother | |
| Brother | Uncle | |
| Sister | Aunt | |
| Offspring | Half sibling | |
| Sub-total | sub-total = | sub-total = |
| | FH total weight score = ___ | |

Model Form 4. Bio-Genetic Criteria Profile Scoring Key

| Individual Chrono Criteria | Determining Total Chrono Criteria Score | Slightly Elevated | Elevated | Highly Elevated | Chronic |
|---|---|---|---|---|---|
| Each criteria has a continuum of severity with assigned numerical weights | The sum of all the qualifying criteria weights equals the total chrono criteria score | Numerical weight = 1 | Numerical Weight = 2 | Numerical Weight = 3 | Numerical weight = 4 |
| 1. BAC | Snapshot in time | .13–.14 | .15–.17 | .18–.21 | .22 or higher |
| 2. Drinking Patterns w/ respect to frequency* | See comments below | n/a | 3 × weekly | 4–7 × weekly | n/a |
| 3. Drinking patterns w/respect to quantity (DPQ) | 'Regularly' is defined as on average, at least one time weekly. | If the BAC level regularly reached is .05 | If the BAC level regularly reached is .06–.07 | If the BAC level regularly reached is .08–.09 | If the BAC level regularly reached is .10 or more |
| 4. Family History of Addictive Disorders | Number of blood relatives on both sides of the family. Direct, less direct and/or Indirect blood lineage | One 'less direct' member (aunt, uncle), or two 'indirect' (cousins) FH score of (.5–.75) | One 'direct' lineage (father/mother, sibling/offspring) or Two 'less direct' members or equiv. FH score of (1–1.25) | One 'direct' lineage with One or two 'less direct' lineages or equiv. FH score of (1.5–2 [w/o two direct]) | More than or equal to, 2 direct lineages FH score of (2 or greater) |
| 5. Blackouts | Particular attn should be paid to frequency and time, >1 hr, several hrs, a day or more | 1 blackout over 10 years ago | 1 blackout w/in last 10 years or 2 blackouts ever | 3–5 blackouts or 2 blackouts within last year | 6 or more or 3–5 within last year |

| Chrono Criteria Scoring Chart | Description | Sub Score |
|---|---|---|
| 1. Drinking patterns with respect to frequency<br>2. Drinking patterns with respect to quantity (DPQ). Applicable only if client drinks at least 1 × weekly (=regular drinker)<br>3. Family history of addictive disorders<br>4. Blood Alc. Concentration (BAC) @ arrest<br>5. Blackouts | Averages ___ beers/drinks over ___ hrs = ___ BAC = avg wkly BAC per sitting | |
| | Total Chrono Criteria Score = ___ | |

4. CHRONIC FAMILY HISTORY (FH) DECISION TREE

Chronic FH is defined as two or more direct Blood lineage. (see 'FH of Addictive Disorder Chart')
With a prior record code of:

| | |
|---|---|
| 3a–3b | Mandates no less than DIN w/AA × 2 for 1–2 yrs |
| 3c–3I | Mandates no less than a level 4 finding |

With a MAST code of:

| | |
|---|---|
| 3a–3b | Mandates no less than Adv. w/AA × 2 for 3 mos - DIN with AA × 2 for 6 mos |
| 3c | No less than DIN w/AA × 2 for 1 yr |
| 3d–3e | No less than DIN w/AA × 2 for 1–2 yrs |
| 3f–3g | a move to level 4 is mandated |

5. CHRONIC DRINKING PATTERN WITH RESPECT TO QUANTITY (DPQ) DECISION TREE

A chronic drinking pattern with respect to quantity (DPQ), defined as, drinking to a BAC of .10 or more on a 1 × weekly or greater basis
With a prior record code of:

| | |
|---|---|
| 3a–3b | Mandates no less than DIN w/AA × 2 for 1–2 yrs |
| 3c–3I | Mandates no less than a level 4 finding |

With a MAST code of:

| | |
|---|---|
| 3a–3b | Mandates no less than Adv. w/AA × 2 for 3 mos - DIN with AA × 2 for 6 mos |
| 3c | No less than DIN w/AA × 2 for 1 yr |
| 3d–3e | No less than DIN w/AA × 2 for 1–2 yrs |
| 3f–3g | a move to level 4 is mandated |

6. PRIOR RECORD COMBINATION CHART DECISION TREES
PR = ____ MAST = ____ DAST = ____
CHRONO CRITERIA SCORE = ____

Prior Record Code (3a–3b) Combination Chart

| With a Prior Record of 3a–3b | MAST Score | DAST Score | Chrono Criteria Score | Recommended Level | Level of Counseling |
|---|---|---|---|---|---|
| Combined with 3a–3b | 4/5* | 4 | 3 | Advanced w/AA × 2 for 3 mos. |
| Combined with 3c | 5 | 5 | 3 | DIN |
| Combined with 3d | 5/6* | 6 | 3 | DIN w/AA × 2 for 6 mos. |
| Combined with 3e | 6 | 7–8 | 3 | DIN w/AA × 2 for 1 yr. |
| Combined with 3f | 6–7 | 9–10 | 3 | DIN w/AA × 2 for 2 yrs. |
| Combined with 3g–4b | 8 | 11 or more | 4 | see level 4 recommendation options |

Prior Record Code (3c–3d) Combination Chart

| With a Prior Record of 3c–3d | MAST Score | DAST Score | Chrono Criteria Score | Recommended Level | Level of Counseling |
|---|---|---|---|---|---|
| Combined with 3a–3b | 4/5* | 4 | 3 | DIN |
| Combined with 3c | 5 | 5 | 3 | DIN w/AA × 2 for 6 mos. |
| Combined with 3d | 5/6* | 6 | 3 | DIN w/AA × 2 for 1 yr. |
| Combined with 3e–3f | 6–7 | 7–8 | 3 | DIN w/AA × 2 for 2 yrs. |
| Combined with 3g–4b | 8 | 9 or more | 4 | see level 4 recommendation options |

Prior Record Code (3e–3f) Combination Chart

| With a Prior Record of 3e–3f | MAST Score | DAST Score | Chrono Criteria Score | Recommended Level | Level of Counseling |
|---|---|---|---|---|---|
| Combined with 3b–3c | 5 | 4 | 3 | DIN w/AA × 2 for 1 yr. |
| Combined with 3d | 6–7 | 5–6 | 3 | DIN w/AA × 2 for 2 yrs. |
| Combined with 3e–4b | 7/8* | 7 or more | 4 | see level 4 recommendation options |

Prior Record Code (3g–3i) Combination Chart

| With a Prior Record of 3g–3i | MAST Score | DAST Score | Chrono Criteria Score | Recommended Level | Level of Counseling |
|---|---|---|---|---|---|
| Combined with 3c | 5–7 | 4 | 3 | DIN w/AA × 2 for 2 yrs. |
| Combined with 3d–4b | 7/8* | 5 or more | 4 | see level 4 recommendation options |

*asterisk indicates if pending drug case is a misd. rather than a felony, then the higher DAST cut-off score is used

7. SASSI DECISION TREE

| | |
|---|---|
| PSA score w/no additional qualifiers | mandates no less than a level 2 finding |
| PSA score w/chrono score of 3 or more | mandates no less than a level 3 finding |
| HPD w/no additional qualifiers | mandates no less than a level 3 finding |

SASSI Combination Chart - Factors combining with HPD on the SASSI that place client at no less than a level 4 finding

| With a HPD finding on the SASSI | MAST Scoring Code | DAST Score | Chrono Criteria Score | Prior Record Code | Family History |
|---|---|---|---|---|---|
| Combined with any of the following place client at no less than a level 4 finding | 3d–3g | 6–7 w/pending felony offense or a prior record code of 3a–3b | 9–11 | 3f–3i | of two direct lineage |

8. NDP DECISION TREE

| | |
|---|---|
| NDP OF 3–4 | mandates no less than a level 2 finding |
| NDP OF 5–7 | mandates no less than a level 3 finding |

9. DAST DECISION TREE

| | |
|---|---|
| DAST of 0–2, or a 3, w/no additional qualifiers | Places client at a level 1 finding |
| DAST of 4–5 | Mandates no less than a level 2 finding |
| DAST of 6–8 | Mandates no less than a level 3 finding |
| DAST of 9–20 | Mandates no less than a level 4–6 finding |

10. MORTIMER FILKINS TEST (MFT) DECISION TREE

| | | |
|---|---|---|
| MFT of 12–16* | mandates no less than a level 2 finding | |
| MFT of 16**–21 | mandates no less than a level 3 finding | no less than Advanced should be recommended |
| MFT of 22 or > | mandates no less than a level 3 finding | no less than DIN w/ or w/o AA should be recommended |

*w/no additional qualifiers
**w/additional qualifiers

11. BLOOD ALCOHOL CONCENTRATION (BAC) DECISION TREE

| | |
|---|---|
| With a BAC level of .15–.19 at time of arrest | mandates no less than a level 2 finding |
| With a BAC level of .20–.26 at time of arrest | mandates no less than a level 3 finding and a recommendation level of Adv. - DIN w/AA × 2 for 1 yr |
| With a BAC level of .27 or higher at time of arrest | mandates no less than a level 4 finding |

12. OTHER SIGNIFICANT CHRONO CRITERIA DECISION TREE

1. Prior Counseling Modalities

A staffing assumption we make is that if client was ever clinically assessed as being chemically dependent and this finding appears to have been clearly an integrible one, then, any future involvement with chemical use that led to an arrest or involvement in the criminal justice system would indicate no less than a level 4 finding.

Therefore, the importance of exploring whether client has had any prior treatment episodes and, if so, whether they were precipitated by an integrible chemical dependency finding.

2. Impaired Control

Inability to consistently predict how much one will consume or episodes of acting outside of one's behavioral value system due to the ingestion or preoccupation with chemicals is a hallmark sign of addictive disorders. If a pattern of impaired control is established in the written biopsychosocial investigation then no less than a level 4 finding is mandated.

3. Continued Use Despite Known Substantial Risk or Adverse Consequences

A key qualification is 'known'; if a client has not been informed that drinking is particularly damaging him due to his/her health condition, or the client is drinking in violation of conditions of a bond release or probation conditions outside his knowledge, then he/she may be guilty of perhaps poor judgement. However if client understands there are substantial risks to his health, finances, freedom, marriage, etc., but continues to use then there is a problem and no less than a level 3 finding with the DIN program recommendation should be the staffing starting point.

4. Other Significant Drug Use

Smoking or IV drug use (non-THC):

at any time in the past places client at no less than level 3 more than 5× in life but less than 1×monthly no less than DIN w/NA/AA ×2 for 1 yr more than 5× in life plus more than 1×monthly places client at no less than level 4

In the absence of a documented history of drug dependence or treatment, more than 5× in life plus more than 1×monthly over the last 6 mos or more, places client at no less than level 4. note: If the frequency of use is closer to 1×monthly then an extended period of time, 6 mos–1 yr is needed to justify a level 4 finding. However, if the frequency is more chronic, time length of pattern becomes less important.

Drug Use w/respect to route of administration and frequency of use. A history of IV drug use or freebasing is a strong indication of no less than a level 4 finding.

APPENDIX I

GENERAL MISCELLANEOUS STAFFING CRITERIA NOTES

General

With an assessment level 3 finding no less than advanced program recommendation is mandated.

Felony Assessment Related

If felony offense is drug related it must be accompanied by a drug abuse problem, i.e. possession for sale and/or non use in the absence of criteria indicating problematic relation would not justify a level 4 finding, nor would it justify recommending mandatory extended AA/NA meetings.

Regarding Drinking Patterns

Drinking frequency is not necessarily a marker for significant tolerance (as opposed to the quantity or the number of drinks per sitting). Continued AOD use patterns subsequent to arrest vs abstinence or drastic reduction in AOD use can be important staffing considerations. Therefore, partial disregard of this issue is appropriate if client has no prior alc/drug related priors nor other significant markers, and has been abstinent or virtually abstinent since arrest. note: young drinkers may drink abusively w/the absence of compulsion. It is often particularly difficult to distinguish between substance abuse or substance dependence in this age group. Therefore special care and considerations should be taken before assessing members of this population as chemically dependent.

Prior Record Related Notes

Whenever pending offense is a pending DWI 2nd, no less than AA ×2 for 1 yr should be included with DIN rec.

With pending felony alc/drug related arrest no less than assessment level 3.

A pending DWI offense that becomes a deferred prosecution should not be given the same staffing weight as a pending DWI (conviction) offense for staffing purposes.

When pending alc. related offense is not a DWI but prior offense was a DWI, reverse pending and prior offense, in order to determine minimum possible assessment level according to the Prior Record Decision Tree.

TABLE I

PROGRAM DESCRIPTIONS OF COUNSELING OPTIONS

Intermediate Groups—Include eight hours of chemical dependency related education and two twelve step meetings (10 hours). The program is appropriate for offenders who are assessed as having no problems outside of the arrest and would benefit from basic education regarding alcohol, other drugs and chemical dependency.

12 Hour DWI Education Class—A twelve hour basic education class on the physical effects of alcohol and other drugs, driving impairment after drinking, traffic safety issues, laws pertaining to DWI and an introduction to chemical dependency. This is a statewide program certified and regulated by the Texas Commission on Alcohol and Drug Abuse (TCADA). It is mandated by law for first time convicted DWI offenders to complete within the first six months of probation to avoid automatic license suspension by the Texas Department of Safety (DPS). The program is also appropriate for other offenders who would benefit from basic education regarding alcohol.

15 Hour Drug Education Class—A 15 hour basic education class to educate drug offenders on the dangers of illicit drug use and abuse. The class enables the offender to gain information on the effects of drug use and related illegal activities on personal, family, social economic and community life, and to develop a plan for positive lifestyle changes to reduce chances of being involved in future drug use and associated illegal behaviors. This is a statewide program certified and regulated by TCADA. It is mandated by law for convicted drug related offenders and enables participants to reinstate their suspended driver's license once the mandatory six month suspension period expires and proof of class completion subsequent to conviction date is provided to DPS with a reinstatement fee. The program is also appropriate for other offenders who were not convicted of an illicit drug related offense but would benefit from basic education regarding drug abuse issues.

Intermediate Program—A program level of 22 hours that include both the Intermediate groups and the 12 hour DWI Education class described above.

Advanced Program—Is a TCADA licensed Supportive Outpatient Level IV Treatment Program consisting of 2 hours of group, eight self-help meetings, journalizing and individual office visits. The program level also includes the 12 hour DWI Education class. This program level consists of 32 counseling/education hours. The program level is for clients assessed at the lower end of the problem but not chemically dependent range. It provides information and group work towards understanding the difference in use, abuse and addiction, the progressionary nature and signs and symptoms of evolving chemical dependency.

DWI Intervention Program (DIN)—This is a 48 hour program that includes 30 hours of group meetings, 18 hours of 12 step meetings and individual counseling sessions all occurring over a nine week period. This is a statewide program certified and regulated by TCADA which is required by offenders convicted of a second DWI offense to get there driver's license reinstated. This program meets twice a week for two hours each night and promotes behavioral change by challenging belief systems, promoting problem solving and coping skill development while dialoguing chemical abuse and addiction issues. The program is appropriate for clients assessed at the higher end of the problem but non chemically dependent range regardless of the referring offense.

Intensive Out Patient Treatment (IOP)—TCADA licensed level III treatment program, generally in the 50–80 hour range of chemical dependency counseling, for clients assessed in the early through mid stage chemical dependency ranges.

In Patient Treatment (IP)—TCADA licensed Level II treatment program, generally a 20–30 day residential treatment stay followed by out patient treatment services. Clients assessed in late stage chemical dependency range or mid level chemical dependency range who have untenable drug using living environment issues.

TABLE II

BAC CALCULATIONS
MALES
(Based on alcohol content of 4.75%) (Jan. 23, 1997)

| | Body weight | | | | | | | | | | | |
|---|---|---|---|---|---|---|---|---|---|---|---|---|
| # of Drinks | 130 | 140 | 150 | 160 | 170 | 180 | 190 | 200 | 220 | 240 | 260 | 280 |

ONE HOUR

| | | | | | | | | | | | | |
|---|---|---|---|---|---|---|---|---|---|---|---|---|
| 1 | 0.016 | 0.014 | 0.012 | 0.01 | 0.009 | 0.008 | 0.007 | 0.006 | 0.004 | 0.002 | 1E-03 | 0 |
| 2 | 0.048 | 0.044 | 0.04 | 0.036 | 0.033 | 0.03 | 0.029 | 0.026 | 0.022 | 0.019 | 0.016 | 0.014 |
| 3 | 0.08 | 0.073 | 0.067 | 0.062 | 0.057 | 0.053 | 0.049 | 0.047 | 0.041 | 0.036 | 0.032 | 0.029 |
| 4 | 0.111 | 0.103 | 0.094 | 0.087 | 0.082 | 0.076 | 0.071 | 0.067 | 0.06 | 0.053 | 0.048 | 0.044 |
| 5 | 0.143 | 0.131 | 0.122 | 0.113 | 0.105 | 0.099 | 0.093 | 0.087 | 0.078 | 0.07 | 0.064 | 0.058 |
| 6 | 0.175 | 0.161 | 0.149 | 0.139 | 0.13 | 0.122 | 0.115 | 0.108 | 0.097 | 0.087 | 0.08 | 0.073 |
| 7 | 0.206 | 0.19 | 0.177 | 0.164 | 0.154 | 0.144 | 0.136 | 0.128 | 0.116 | 0.105 | 0.095 | 0.087 |
| 8 | 0.238 | 0.219 | 0.204 | 0.19 | 0.179 | 0.167 | 0.158 | 0.149 | 0.134 | 0.122 | 0.111 | 0.103 |
| 9 | 0.269 | 0.249 | 0.232 | 0.216 | 0.202 | 0.19 | 0.18 | 0.17 | 0.153 | 0.139 | 0.127 | 0.117 |
| 10 | 0.301 | 0.278 | 0.258 | 0.241 | 0.226 | 0.213 | 0.201 | 0.19 | 0.172 | 0.156 | 0.143 | 0.131 |
| 11 | 0.333 | 0.308 | 0.286 | 0.267 | 0.251 | 0.236 | 0.222 | 0.211 | 0.19 | 0.173 | 0.159 | 0.146 |
| 12 | 0.364 | 0.337 | 0.314 | 0.293 | 0.275 | 0.258 | 0.244 | 0.232 | 0.209 | 0.19 | 0.175 | 0.161 |

TWO HOURS

| | | | | | | | | | | | | |
|---|---|---|---|---|---|---|---|---|---|---|---|---|
| 1 | 0 | 0 | 0 | 0 | 0 | 0 | 0 | 0 | 0 | 0 | 0 | 0 |
| 2 | 0.033 | 0.029 | 0.025 | 0.021 | 0.018 | 0.015 | 0.013 | 0.01 | 0.007 | 0.004 | 1E-03 | 0 |
| 3 | 0.065 | 0.058 | 0.052 | 0.047 | 0.042 | 0.038 | 0.034 | 0.031 | 0.026 | 0.021 | 0.017 | 0.013 |
| 4 | 0.096 | 0.087 | 0.079 | 0.072 | 0.067 | 0.061 | 0.056 | 0.052 | 0.045 | 0.038 | 0.033 | 0.029 |
| 5 | 0.127 | 0.116 | 0.106 | 0.096 | 0.09 | 0.084 | 0.078 | 0.072 | 0.063 | 0.055 | 0.048 | 0.043 |
| 6 | 0.16 | 0.145 | 0.134 | 0.124 | 0.115 | 0.106 | 0.1 | 0.093 | 0.082 | 0.072 | 0.065 | 0.058 |
| 7 | 0.191 | 0.175 | 0.162 | 0.149 | 0.139 | 0.129 | 0.121 | 0.113 | 0.101 | 0.089 | 0.08 | 0.072 |
| 8 | 0.222 | 0.204 | 0.189 | 0.175 | 0.163 | 0.152 | 0.143 | 0.134 | 0.119 | 0.106 | 0.096 | 0.087 |
| 9 | 0.254 | 0.234 | 0.217 | 0.2 | 0.187 | 0.175 | 0.164 | 0.155 | 0.138 | 0.124 | 0.112 | 0.102 |
| 10 | 0.286 | 0.263 | 0.243 | 0.226 | 0.211 | 0.198 | 0.186 | 0.175 | 0.157 | 0.141 | 0.127 | 0.116 |
| 11 | 0.317 | 0.293 | 0.271 | 0.252 | 0.236 | 0.22 | 0.207 | 0.196 | 0.175 | 0.158 | 0.143 | 0.131 |
| 12 | 0.349 | 0.322 | 0.298 | 0.277 | 0.259 | 0.243 | 0.229 | 0.217 | 0.194 | 0.175 | 0.16 | 0.145 |

TABLE III

BAC CALCULATIONS

| | Body weight | | | | | | | | | | | |
|---|---|---|---|---|---|---|---|---|---|---|---|---|
| # of Drinks | 130 | 140 | 150 | 160 | 170 | 180 | 190 | 200 | 220 | 240 | 260 | 280 |

THREE HOURS

| | | | | | | | | | | | | |
|---|---|---|---|---|---|---|---|---|---|---|---|---|
| 1 | 0 | 0 | 0 | 0 | 0 | 0 | 0 | 0 | 0 | 0 | 0 | 0 |
| 2 | 0.018 | 0.013 | 0.01 | 0.006 | 0.003 | 0 | 0 | 0 | 0 | 0 | 0 | 0 |
| 3 | 0.049 | 0.043 | 0.037 | 0.031 | 0.027 | 0.023 | 0.019 | 0.016 | 0.01 | 0.006 | 0.002 | 0 |
| 4 | 0.081 | 0.072 | 0.637 | 0.057 | 0.051 | 0.046 | 0.041 | 0.037 | 0.029 | 0.023 | 0.018 | 0.013 |
| 5 | 0.112 | 0.101 | 0.091 | 0.083 | 0.075 | 0.068 | 0.063 | 0.057 | 0.048 | 0.04 | 0.033 | 0.028 |
| 6 | 0.144 | 0.13 | 0.119 | 0.108 | 0.1 | 0.091 | 0.085 | 0.078 | 0.067 | 0.057 | 0.049 | 0.043 |
| 7 | 0.176 | 0.16 | 0.146 | 0.134 | 0.124 | 0.114 | 0.105 | 0.098 | 0.086 | 0.074 | 0.065 | 0.057 |
| 8 | 0.207 | 0.189 | 0.174 | 0.16 | 0.148 | 0.137 | 0.127 | 0.119 | 0.104 | 0.091 | 0.081 | 0.072 |
| 9 | 0.238 | 0.219 | 0.201 | 0.185 | 0.172 | 0.16 | 0.149 | 0.14 | 0.123 | 0.108 | 0.097 | 0.086 |
| 10 | 0.271 | 0.248 | 0.228 | 0.211 | 0.196 | 0.182 | 0.171 | 0.16 | 0.142 | 0.125 | 0.112 | 0.101 |
| 11 | 0.302 | 0.277 | 0.256 | 0.237 | 0.22 | 0.205 | 0.192 | 0.181 | 0.16 | 0.143 | 0.128 | 0.116 |
| 12 | 0.333 | 0.307 | 0.283 | 0.262 | 0.244 | 0.228 | 0.214 | 0.201 | 0.179 | 0.16 | 0.144 | 0.13 |

FOUR HOURS

| | | | | | | | | | | | | |
|---|---|---|---|---|---|---|---|---|---|---|---|---|
| 1 | 0 | 1 | 2 | 3 | 4 | 5 | 6 | 7 | 8 | 9 | 10 | 11 |
| 2 | 0.003 | 0 | 0 | 0 | 0 | 0 | 0 | 0 | 0 | 0 | 0 | 0 |
| 3 | 0.034 | 0.028 | 0.022 | 0.016 | 0.011 | 0.008 | 0.004 | 1E-03 | 0 | 0 | 0 | 0 |
| 4 | 0.066 | 0.057 | 0.048 | 0.042 | 0.036 | 0.03 | 0.026 | 0.022 | 0.014 | 0.008 | 0.003 | 0 |
| 5 | 0.097 | 0.086 | 0.076 | 0.067 | 0.06 | 0.053 | 0.048 | 0.042 | 0.032 | 0.025 | 0.018 | 0.012 |
| 6 | 0.129 | 0.115 | 0.104 | 0.093 | 0.085 | 0.076 | 0.069 | 0.063 | 0.051 | 0.042 | 0.034 | 0.028 |
| 7 | 0.161 | 0.144 | 0.131 | 0.119 | 0.108 | 0.099 | 0.09 | 0.083 | 0.07 | 0.059 | 0.049 | 0.042 |
| 8 | 0.192 | 0.174 | 0.13 | 0.144 | 0.133 | 0.122 | 0.112 | 0.104 | 0.088 | 0.076 | 0.066 | 0.057 |
| 9 | 0.223 | 0.203 | 0.186 | 0.17 | 0.128 | 0.144 | 0.134 | 0.124 | 0.107 | 0.093 | 0.082 | 0.071 |
| 10 | 0.256 | 0.233 | 0.213 | 0.198 | 0.181 | 0.167 | 0.156 | 0.144 | 0.126 | 0.11 | 0.097 | 0.086 |
| 11 | 0.287 | 0.262 | 0.24 | 0.221 | 0.205 | 0.19 | 0.177 | 0.165 | 0.144 | 0.127 | 0.113 | 0.101 |
| 12 | 0.318 | 0.292 | 0.268 | 0.247 | 0.229 | 0.213 | 0.199 | 0.186 | 0.163 | 0.144 | 0.129 | 0.115 |

TABLE IV

BAC CALCULATIONS

| | Body weight | | | | | | | | | | | |
|---|---|---|---|---|---|---|---|---|---|---|---|---|
| # of Drinks | 130 | 140 | 150 | 160 | 170 | 180 | 190 | 200 | 220 | 240 | 260 | 280 |
| FIVE HOURS | | | | | | | | | | | | |
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0.019 | 0.012 | 0.007 | 1E-03 | 0 | 0 | 0 | 0 | 0 | 0 | 0 | 0 |
| 4 | 0.05 | 0.042 | 0.033 | 0.027 | 0.021 | 0.015 | 0.01 | 0.007 | 0 | 0 | 0 | 0 |
| 5 | 0.082 | 0.07 | 0.061 | 0.052 | 0.07 | 0.038 | 0.032 | 0.027 | 0.017 | 0.01 | 0.003 | 0 |
| 6 | 0.114 | 0.1 | 0.088 | 0.078 | 0.069 | 0.061 | 0.054 | 0.048 | 0.036 | 0.027 | 0.019 | 0.012 |
| 7 | 0.145 | 0.129 | 0.116 | 0.104 | 0.093 | 0.084 | 0.075 | 0.067 | 0.055 | 0.044 | 0.342 | 0.027 |
| 8 | 0.177 | 0.159 | 0.143 | 0.129 | 0.118 | 0.106 | 0.097 | 0.088 | 0.073 | 0.061 | 0.504 | 0.042 |
| 9 | 0.208 | 0.188 | 0.171 | 0.155 | 0.142 | 0.129 | 0.119 | 0.109 | 0.092 | 0.078 | 0.665 | 0.056 |
| 10 | 0.24 | 0.218 | 0.198 | 0.181 | 0.165 | 0.152 | 0.141 | 0.129 | 0.111 | 0.095 | 0.082 | 0.07 |
| 11 | 0.272 | 0.247 | 0.225 | 0.206 | 0.19 | 0.175 | 0.162 | 0.15 | 0.129 | 0.112 | 0.098 | 0.086 |
| 12 | 0.303 | 0.276 | 0.253 | 0.232 | 0.214 | 0.198 | 0.183 | 0.171 | 0.148 | 0.129 | 0.114 | 0.1 |
| SIX HOURS | | | | | | | | | | | | |
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0.004 | 0 | 0 | 0 | 0 | 0 | 0 | 0 | 0 | 0 | 0 | 0 |
| 4 | 0.035 | 0.027 | 0.018 | 0.011 | 0.006 | 0 | 0 | 0 | 0 | 0 | 0 | 0 |
| 5 | 0.067 | 0.055 | 0.046 | 0.037 | 0.029 | 0.023 | 0.017 | 0.011 | 0.002 | 0 | 0 | 0 |
| 6 | 0.099 | 0.085 | 0.073 | 0.063 | 0.054 | 0.046 | 0.039 | 0.032 | 0.021 | 0.011 | 0.004 | 0 |
| 7 | 0.13 | 0.114 | 0.101 | 0.088 | 0.078 | 0.068 | 0.06 | 0.052 | 0.04 | 0.029 | 0.019 | 0.011 |
| 8 | 0.162 | 0.143 | 0.128 | 0.114 | 0.103 | 0.091 | 0.082 | 0.073 | 0.058 | 0.046 | 0.035 | 0.027 |
| 9 | 0.193 | 0.173 | 0.156 | 0.14 | 0.126 | 0.114 | 0.104 | 0.094 | 0.076 | 0.063 | 0.051 | 0.041 |
| 10 | 0.225 | 0.202 | 0.182 | 0.165 | 0.15 | 0.137 | 0.125 | 114 | 0.096 | 0.08 | 0.067 | 0.055 |
| 11 | 0.257 | 0.232 | 0.21 | 0.191 | 0.175 | 0.131 | 0.146 | 0.135 | 0.114 | 0.097 | 0.083 | 0.07 |
| 12 | 0.288 | 0.261 | 0.238 | 0.217 | 0.199 | 0.182 | 0.168 | 0.156 | 0.133 | 0.114 | 0.099 | 0.085 |

TABLE V

BAC CALCULATIONS
Female (Jan. 23, 1997)
(Based on alcohol content of 4.75%)

| | Body weight | | | | | | | | | | |
|---|---|---|---|---|---|---|---|---|---|---|---|
| # of Drinks | 100 | 110 | 120 | 130 | 140 | 150 | 160 | 170 | 180 | 190 | 200 |
| ONE HOUR | | | | | | | | | | | |
| 1 | 0.034 | 0.029 | 0.026 | 0.023 | 0.02 | 0.018 | 0.015 | 0.014 | 0.012 | 0.01 | 0.01 |
| 2 | 0.084 | 0.074 | 0.067 | 0.061 | 0.055 | 0.05 | 0.047 | 0.043 | 0.04 | 0.037 | 0.034 |
| 3 | 0.133 | 0.12 | 0.108 | 0.099 | 0.09 | 0.084 | 0.077 | 0.072 | 0.067 | 0.063 | 0.059 |
| 4 | 0.182 | 0.164 | 0.149 | 0.137 | 0.125 | 0.116 | 0.108 | 0.101 | 0.094 | 0.088 | 0.084 |
| 5 | 0.232 | 0.209 | 0.19 | 0.175 | 0.161 | 0.149 | 0.139 | 0.13 | 0.122 | 0.115 | 0.108 |
| 6 | 0.28 | 0.254 | 0.232 | 0.213 | 0.196 | 0.182 | 0.17 | 0.159 | 0.149 | 0.141 | 0.133 |
| 7 | 0.33 | 0.298 | 0.273 | 0.25 | 0.232 | 0.215 | 0.2 | 0.188 | 0.177 | 0.166 | 0.158 |
| 8 | 0.379 | 0.343 | 0.314 | 0.288 | 0.267 | 0.248 | 0.232 | 0.217 | 0.204 | 0.193 | 0.182 |
| 9 | 0.428 | 0.389 | 0.354 | 0.326 | 0.302 | 0.28 | 0.262 | 0.246 | 0.232 | 0.219 | 0.207 |
| 10 | 0.478 | 0.433 | 0.396 | 0.364 | 0.337 | 0.314 | 0.293 | 0.275 | 0.258 | 0.244 | 0.232 |
| 11 | 0.527 | 0.478 | 0.437 | 0.402 | 0.372 | 0.347 | 0.324 | 0.304 | 0.286 | 0.27 | 0.256 |
| 12 | 0.577 | 0.523 | 0.478 | 0.44 | 0.408 | 0.379 | 0.354 | 0.333 | 0.314 | 0.296 | 0.28 |
| TWO HOUR | | | | | | | | | | | |
| 1 | 0.019 | 0.014 | 0.01 | 0.008 | 0.005 | 0.003 | 0 | 0 | 0 | 0 | 0 |
| 2 | 0.068 | 0.059 | 0.052 | 0.046 | 0.04 | 0.035 | 0.031 | 0.028 | 0.025 | 0.219 | 0.19 |
| 3 | 0.118 | 0.105 | 0.093 | 0.084 | 0.075 | 0.068 | 0.062 | 0.057 | 0.052 | 0.475 | 0.437 |
| 4 | 0.167 | 0.149 | 0.134 | 0.122 | 0.11 | 0.101 | 0.093 | 0.086 | 0.079 | 0.073 | 0.684 |
| 5 | 0.217 | 0.194 | 0.175 | 0.16 | 0.145 | 0.134 | 0.124 | 0.115 | 0.106 | 0.1 | 0.093 |
| 6 | 0.265 | 0.238 | 0.217 | 0.198 | 0.181 | 0.167 | 0.155 | 0.143 | 0.134 | 0.125 | 0.118 |
| 7 | 0.314 | 0.283 | 0.257 | 0.235 | 0.217 | 0.2 | 0.185 | 0.173 | 0.162 | 0.151 | 0.143 |
| 8 | 0.364 | 0.328 | 0.298 | 0.273 | 0.252 | 0.233 | 0.217 | 0.201 | 0.189 | 0.178 | 0.167 |
| 9 | 0.413 | 0.373 | 0.339 | 0.311 | 0.287 | 0.265 | 0.247 | 0.231 | 0.217 | 0.203 | 0.192 |
| 10 | 0.463 | 0.418 | 0.381 | 0.349 | 0.322 | 0.298 | 0.277 | 0.259 | 0.243 | 0.229 | 0.217 |
| 11 | 0.512 | 0.463 | 0.422 | 0.387 | 0.357 | 0.332 | 0.309 | 0.289 | 0.271 | 0.255 | 0.24 |
| 12 | 0.561 | 0.507 | 0.463 | 0.425 | 0.392 | 0.364 | 0.339 | 0.317 | 0.298 | 0.281 | 0.265 |

TABLE VI

BAC CALCULATIONS

| # of Drinks | \multicolumn{11}{c}{Body weight} |
|---|---|---|---|---|---|---|---|---|---|---|---|
|  | 100 | 110 | 120 | 130 | 140 | 150 | 160 | 170 | 180 | 190 | 200 |
| \multicolumn{12}{c}{THREE HOUR} |
| 1 | 0.004 | 0 | 0 | 0 | 0 | 0 | 0 | 0 | 0 | 0 | 0 |
| 2 | 0.053 | 0.044 | 0.037 | 0.03 | 0.025 | 0.02 | 0.162 | 0.012 | 0.01 | 0.007 | 0.004 |
| 3 | 0.103 | 0.089 | 0.078 | 0.068 | 0.06 | 0.053 | 0.047 | 0.042 | 0.037 | 0.032 | 0.029 |
| 4 | 0.152 | 0.134 | 0.119 | 0.106 | 0.095 | 0.086 | 0.078 | 0.07 | 0.064 | 0.058 | 0.053 |
| 5 | 0.201 | 0.179 | 0.16 | 0.144 | 0.13 | 0.119 | 0.108 | 0.1 | 0.091 | 0.085 | 0.078 |
| 6 | 0.25 | 0.223 | 0.201 | 0.182 | 0.165 | 0.152 | 0.14 | 0.128 | 0.119 | 0.11 | 0.103 |
| 7 | 0.299 | 0.268 | 0.242 | 0.219 | 0.201 | 0.184 | 0.17 | 0.158 | 0.146 | 0.136 | 0.127 |
| 8 | 0.349 | 0.313 | 0.283 | 0.257 | 0.237 | 0.218 | 0.201 | 0.186 | 0.174 | 0.162 | 0.152 |
| 9 | 0.398 | 0.358 | 0.324 | 0.295 | 0.272 | 0.25 | 0.232 | 0.216 | 0.201 | 0.188 | 0.177 |
| 10 | 0.447 | 0.403 | 0.366 | 0.333 | 0.307 | 0.283 | 0.262 | 0.244 | 0.228 | 0.214 | 0.201 |
| 11 | 0.497 | 0.447 | 0.407 | 0.371 | 0.342 | 0.316 | 0.294 | 0.274 | 0.256 | 0.239 | 0.225 |
| 12 | 0.546 | 0.492 | 0.447 | 0.409 | 0.377 | 0.349 | 0.324 | 0.302 | 0.283 | 0.266 | 0.25 |
| \multicolumn{12}{c}{FOUR HOURS} |
| 1 | 0 | 0 | 0 | 0 | 0 | 0 | 0 | 0 | 0 | 0 | 0 |
| 2 | 0.038 | 0.029 | 0.022 | 0.152 | 0.01 | 0.005 | 1E-03 | 0 | 0 | 0 | 0 |
| 3 | 0.087 | 0.074 | 0.063 | 0.053 | 0.045 | 0.038 | 0.031 | 0.027 | 0.022 | 0.017 | 0.133 |
| 4 | 0.137 | 0.119 | 0.104 | 0.091 | 0.08 | 0.07 | 0.063 | 0.055 | 0.048 | 0.043 | 0.038 |
| 5 | 0.186 | 0.163 | 0.144 | 0.129 | 0.115 | 0.104 | 0.093 | 0.085 | 0.076 | 0.069 | 0.063 |
| 6 | 0.235 | 0.208 | 0.186 | 0.167 | 0.15 | 0.137 | 0.124 | 0.113 | 0.104 | 0.095 | 0.087 |
| 7 | 0.284 | 0.253 | 0.227 | 0.204 | 0.186 | 0.169 | 0.155 | 0.143 | 0.131 | 0.121 | 0.112 |
| 8 | 0.333 | 0.297 | 0.268 | 0.242 | 0.221 | 0.202 | 0.186 | 0.171 | 0.159 | 0.147 | 0.137 |
| 9 | 0.383 | 0.343 | 0.309 | 0.28 | 0.257 | 0.235 | 0.217 | 0.2 | 0.186 | 0.173 | 0.162 |
| 10 | 0.432 | 0.388 | 0.351 | 0.318 | 0.292 | 0.268 | 0.247 | 0.229 | 0.213 | 0.199 | 0.186 |
| 11 | 0.482 | 0.432 | 0.391 | 0.356 | 0.327 | 0.301 | 0.278 | 0.258 | 0.24 | 0.224 | 0.21 |
| 12 | 0.531 | 0.477 | 0.432 | 0.394 | 0.362 | 0.333 | 0.309 | 0.287 | 0.268 | 0.251 | 0.235 |

TABLE VII

BAC CALCULATIONS

| # of Drinks | \multicolumn{11}{c}{Body weight} |
|---|---|---|---|---|---|---|---|---|---|---|---|
|  | 100 | 110 | 120 | 130 | 140 | 150 | 160 | 170 | 180 | 190 | 200 |
| \multicolumn{12}{c}{FIVE HOURS} |
| 1 | 0 | 0 | 0 | 0 | 0 | 0 | 0 | 0 | 0 | 0 | 0 |
| 2 | 0.023 | 0.013 | 0.007 | 0 | 0 | 0 | 0 | 0 | 0 | 0 | 0 |
| 3 | 0.072 | 0.059 | 0.048 | 0.038 | 0.029 | 0.023 | 0.016 | 0.011 | 0.007 | 0.002 | 0 |
| 4 | 0.122 | 0.104 | 0.088 | 0.076 | 0.065 | 0.055 | 0.048 | 0.04 | 0.033 | 0.028 | 0.228 |
| 5 | 0.171 | 0.148 | 0.129 | 0.114 | 0.1 | 0.088 | 0.078 | 0.069 | 0.061 | 0.054 | 0.048 |
| 6 | 0.219 | 0.193 | 0.171 | 0.152 | 0.135 | 0.122 | 0.109 | 0.098 | 0.088 | 0.08 | 0.072 |
| 7 | 0.269 | 0.238 | 0.212 | 0.189 | 0.171 | 0.154 | 0.14 | 0.127 | 0.116 | 0.105 | 0.097 |
| 8 | 0.318 | 0.282 | 0.253 | 0.227 | 0.206 | 0.187 | 0.171 | 0.156 | 0.143 | 0.132 | 0.122 |
| 9 | 0.368 | 0.328 | 0.294 | 0.265 | 0.241 | 0.219 | 0.201 | 0.185 | 0.171 | 0.158 | 0.146 |
| 10 | 0.417 | 0.372 | 0.508 | 0.303 | 0.276 | 0.253 | 0.232 | 0.214 | 0.198 | 0.183 | 0.171 |
| 11 | 0.466 | 0.417 | 0.376 | 0.341 | 0.312 | 0.286 | 0.263 | 0.243 | 0.225 | 0.209 | 0.195 |
| 12 | 0.516 | 0.462 | 0.417 | 0.379 | 0.347 | 0.318 | 0.294 | 0.272 | 0.253 | 0.236 | 0.219 |
| \multicolumn{12}{c}{SIX HOURS} |
| 1 | 0 | 0 | 0 | 0 | 0 | 0 | 0 | 0 | 0 | 0 | 0 |
| 2 | 0.008 | 0 | 0 | 0 | 0 | 0 | 0 | 0 | 0 | 0 | 0 |
| 3 | 0.057 | 0.044 | 0.032 | 0.023 | 0.014 | 0.008 | 1E-03 | 0 | 0 | 0 | 0 |
| 4 | 0.106 | 0.088 | 0.073 | 0.061 | 0.049 | 0.04 | 0.032 | 0.025 | 0.018 | 0.012 | 0.008 |
| 5 | 0.156 | 0.133 | 0.114 | 0.099 | 0.085 | 0.073 | 0.063 | 0.054 | 0.046 | 0.039 | 0.032 |
| 6 | 0.204 | 0.178 | 0.127 | 0.137 | 0.12 | 0.106 | 0.094 | 0.083 | 0.073 | 0.065 | 0.057 |
| 7 | 0.254 | 0.222 | 0.197 | 0.174 | 0.156 | 0.139 | 0.124 | 0.112 | 0.101 | 0.09 | 0.082 |
| 8 | 0.303 | 0.267 | 0.238 | 0.212 | 0.191 | 0.172 | 0.156 | 0.141 | 0.128 | 0.117 | 0.106 |
| 9 | 0.352 | 0.313 | 0.278 | 0.25 | 0.226 | 0.204 | 0.186 | 0.17 | 0.156 | 0.143 | 0.131 |
| 10 | 0.402 | 0.357 | 0.32 | 0.288 | 0.261 | 0.238 | 0.217 | 0.199 | 0.182 | 0.168 | 155.8 |
| 11 | 0.451 | 0.402 | 0.361 | 0.326 | 0.296 | 0.271 | 0.248 | 0.228 | 0.21 | 0.194 | 0.18 |
| 12 | 0.501 | 0.447 | 0.402 | 0.364 | 0.332 | 0.303 | 0.278 | 0.257 | 0.238 | 0.22 | 0.204 |

What is claimed is:

1. A method of evaluating the severity of non-addictive and addictive psychoactive chemical relationships when evaluating a subject's relationship with mood altering chemicals, comprising the steps of:
   (a) evaluating the subject's prior criminal arrest record, if any, and assigning a weighted numerical value thereto,
   (b) evaluating the frequency of chemical use and the negative symptomatology related to the subject's developed tolerance levels to mood altering chemicals, if any, and assigning a weighted numerical value thereto;
   (c) evaluating potential biogenetic predisposition factors, if any, and assigning a weighted numerical value thereto; and
   (d) assigning a diagnostic assessment score to the subject based on the foregoing weighted values;
   wherein the diagnostic assessment score represents a diagnostic placement of the subject within a classification system that corresponds to the severity of both non-addictive and addictive psychoactive chemical relationships that comprise a chemical use/misuse continuum.

2. The method of claim 1, wherein said classification system comprises six primary levels.

3. The method of claim 1, wherein said diagnostic placement further reflects placement in a subcategory within said six-level classification system.

4. The method of claim 1, wherein said diagnostic placement corresponds to the subject's risk to self or society.

5. A method of evaluating the severity of non-addictive and addictive psychoactive chemical relationships when evaluating a subject's relationship with mood altering chemicals, comprising the steps of:
   (a) evaluating the subject's prior criminal arrest record, if any, and assigning a weighted numerical value thereto,
   (b) evaluating the frequency of chemical use and the negative symptomatology related to the subject's developed tolerance levels to mood altering chemicals, if any, and assigning a weighted numerical value thereto;
   (c) evaluating potential biogenetic predisposition factors, if any, and assigning a weighted numerical value thereto; and
   (d) assigning a diagnostic assessment score to the subject based on the foregoing weighted values; wherein each weighted numerical value is determined through the use of one or more decision trees.

6. A method of evaluating the severity of non-addictive and addictive psychoactive chemical relationships when evaluating a subject's relationship with mood altering chemicals, comprising the steps of:
   (a) evaluating the subject's prior criminal arrest record, if any, and assigning a weighted numerical value thereto,
   (b) evaluating the frequency of chemical use and the negative symptomatology related to the subject's developed tolerance levels to mood altering chemicals, if any, and assigning a weighted numerical value thereto;
   (c) evaluating potential biogenetic predisposition factors, if any, and assigning a weighted numerical value thereto; and
   (d) assigning a diagnostic assessment score to the subject based on the foregoing weighted values; wherein each weighted numerical value is determined through the use of one or more screening instruments.

7. The method of claim 1, 5, or 6, further comprising the step of evaluating the subject's prior and/or current chemical use history, if any, and assigning a weighted value thereto prior to step (d).

8. The method of claim 1, 5, or 6, further comprising the step of evaluating negative symptomatology, if any, related to the subject's medical, psychological, social and spiritual profile and assigning a staffing weight value thereto prior to step (d).

9. The method of claim 1, 5, or 6, wherein the evaluation of the subject's prior criminal arrest record, if any, involves an evaluation of the existence of AOD related tickets and arrests, with respect to number, age, severity, and final disposition of the criminal justice involvement.

10. The method of claim 1, 5, or 6, wherein the step evaluating the negative symptomatology related to the subject's developed tolerance levels to mood altering chemicals, if any, is based on an exploration of tolerance issues relative to chemical using patterns both with respect to frequency and quantity per sitting, blood alcohol concentration at arrest, as well as the extent of blackout history.

11. The method of claim 1, 5, or 6, wherein the evaluation of the subject's biogenetic predisposition and symptomatology related to the subject's medical, psychological, social, and spiritual profile is based on bio-psycho-social-spiritual interview of the subject and appropriate exploration of qualifying screening tool responses relative to these issues.

* * * * *